US008088372B2

(12) United States Patent
Hosokawa et al.

(10) Patent No.: US 8,088,372 B2
(45) Date of Patent: Jan. 3, 2012

(54) THROMBIN MUTANT

(75) Inventors: Kazuya Hosokawa, Tokyo (JP); Tomoko Wada, Tokyo (JP)

(73) Assignees: Chisso Corporation, Osaka (JP); Fujimori Kogyo Co., Ltd., Tokyo (JP)

( * ) Notice: Subject to any disclaimer, the term of this patent is extended or adjusted under 35 U.S.C. 154(b) by 61 days.

(21) Appl. No.: 12/514,735

(22) PCT Filed: Nov. 15, 2007

(86) PCT No.: PCT/JP2007/072169
§ 371 (c)(1),
(2), (4) Date: May 13, 2009

(87) PCT Pub. No.: WO2008/059917
PCT Pub. Date: May 22, 2008

(65) Prior Publication Data
US 2010/0040597 A1    Feb. 18, 2010

(30) Foreign Application Priority Data

Nov. 15, 2006 (JP) ................................. 2006-309007

(51) Int. Cl.
*A61K 38/48* (2006.01)
(52) U.S. Cl. ..................... 424/94.64; 424/94.6; 530/350
(58) Field of Classification Search ........................ None
See application file for complete search history.

(56) References Cited

U.S. PATENT DOCUMENTS

| 5,256,766 A | 10/1993 | Coughlin |
| 2007/0282095 A1 | 12/2007 | Hosokawa et al. |

FOREIGN PATENT DOCUMENTS

| WO | WO 92/14750 | 9/1992 |
| WO | WO 95/13385 | 5/1995 |
| WO | WO 96/41868 | 12/1996 |
| WO | WO 2005/089070 | 9/2005 |

OTHER PUBLICATIONS

Supplementary European Search Report dated Feb. 23, 2010.
Myles, Timothy et al., "Structural requirements for the activation of human factor VIII by thrombin", *Blood*, vol. 100, No. 8, Oct. 15, 2002, pp. 2820-2826.
Tsiang, Manuel et al., "Functional requirements for inhibition of thrombin by antithrombin III in the presence and absence of heparin", *The Journal of Biological Chemistry*, vol. 272, No. 18, May 2, 1997, pp. 12024-12029.
PCT/JP2007/072169 International Search Report dated Feb. 26, 2008.
Arcone, R., et al., "Thrombin mutants with altered enzymatic activity have an impaired mitogenic effect on mouse fibroblasts and are inefficient modulators of stellation of rat cortical astrocytes", *Biochim. Biophys. Acta*, 1999, vol. 1451, pp. 173-186.
Bar-Shavit, R., et al., "An Arg-Gly-Asp sequence within thrombin promotes endothelial cell adhesion", *J. Cell Biol.*, 1991, vol. 112:2, pp. 335-344.
Cantwell, A., et al., "Rational design of a potent anticoagulant thrombin", J. Biol. Chem., 2000, vol. 275:51, pp. 39827-39830.
Carter, W.J., et al., "Crystal structure of anticoagulant thrombin variant E217K provides insights into thrombin allostery", *J. Biol. Chem.*, 2004, vol. 279:25, pp. 26387-26394.
Crago, A.M., et al., "Monocyte chemoattractant activity of Ser195 →Ala active site mutant recombinant alpha-thrombin", *Exp. Cell Res.*, 1995, vol. 219:2, pp. 650-656. (Abstract Only).
Gruber, A., et al., "The thrombin mutant W215A/E217A shows safe and potent anticoagulant and antithrombotic effects in vivo", *J. Biol. Chem.*, 2002, vol. 277:31, pp. 27581-27584.
Hall, S.W., et al., "Thrombin interacts with thrombomodulin, protein C, and thrombin-activatable fibrinolysis inhibitor via specific and distinct domains", *J. Biol. Chem.*, 1999, vol. 274:36, pp. 25510-25516.
Harmon, J.T., et al., "Activation of platelets by alpha-thrombin is a receptor-mediated event", *J. Biol. Chem.*, 1986, vol. 261:34, pp. 15928-15933.
Li, C.Q., et al., "Platelet glycoprotein Ib alpha binds to thrombin anion-binding exosite II inducing allosteric changes in the activity of thrombin", *J. Biol. Chem.*, 2001, vol. 276:9, pp. 6161-6168.
Sabo, T.M., et al., "Conformational analysis of gamma' peptide (410-427) interactions thrombin anion binding exosite II", *Biochemistry*, 2006, vol. 45, pp. 7434-7445.
PCT/JP2007/072169 Translation of the IPRP dated Jun. 4, 2009.
Suzuki, K., et al., "Thrombin: Structure-function relationship", *Japanese Journal of Thrombosis and Hemostasis*, vol. 10, Nos. 2 and 3, 1999, pp. 195-203.
Voet, D., et al., *Biochemistry*, vol. 1, 1996, pp. 331-341 and pp. 348-349, Tokyo Kagaku Dozin, Co., Ltd.

*Primary Examiner* — Hope Robinson
(74) *Attorney, Agent, or Firm* — Kilpatrick Townsend & Stockton LLP

(57) ABSTRACT

A thrombin mutant in which at least serine at position 205 among amino acids in the active center of the thrombin B chain has been replaced with another amino acid, and further at least one of the following replacements have been introduced: (I) replacement of arginine at position 89 in the B-chain with another amino acid; (II) replacement of threonine at position 69 or serine at position 22 in the B-chain with another amino acid; (III) replacement of alanine at position 200 in the B-chain with another amino acid; and (IV) replacement of lysine at position 65 in the B-chain with threonine.

16 Claims, No Drawings

THROMBIN MUTANT

PRIOR RELATED APPLICATIONS

The present application is a 35 U.S.C. §371 National Phase filing of PCT application No. PCT/JP2007/072169, filed Nov. 15, 2007, which claims priority to Japanese patent application No. 2006-309007, filed Nov. 15, 2006, each of which is incorporated by reference in its entirety.

TECHNICAL FIELD

The present invention relates to a technology that optimizes an amino acid sequence of an inactivated thrombin mutant having an antithrombotic ability to improve the antithrombotic ability.

BACKGROUND ART

Most of vascular disorders in a brain or a heart are thrombosis, which is mainly caused by abnormality of blood flow, abnormality of coagulation components, and abnormality of a vascular endothelium. Actually, integral action of those abnormalities induces thrombosis. It is thrombin as a serine protease that is involved in all abnormalities and plays a central role in thrombus formation. The thrombin produces a fibrin clump at the final stage of coagulation cascade, and simultaneously accelerates the coagulation cascade by activating XI, V, and VIII factors. In addition, thrombin causes platelet aggregation and activation of endothelial cells through PAR1 which is a thrombin receptor on the platelet and the vascular endothelium. It is reported that the activation of endothelial cells causes the hypercoagulation of a vascular wall and then thrombus formation proceeds, as a result of negative chain Non-patent Document 1).

Non-patent Document 2 describes that an exocite I region plays an important role in substrate recognition which is involved in the main blood coagulation pathway of thrombin. Non-patent Document 3 describes that: a serine protease such as thrombin has serine, histidine, and aspartic acid at the active center; the protease activity is expressed by a charge relay system of those three amino acids; and glycine 193 (the number 193 refers to a position of the amino acid in chymotrypsinogen, and glycine 193 corresponds to glycine at position 203 in thrombin B chain) is involved in the progress from a Michaelis complex to a tetrahedral complex.

Thrombin mutants having amino acid substitutions have been studied. There have been some investigations, as described below, on recombinants in which an amino acid in the active center is replaced as a result of gene recombination of thrombin. For example, Non-patent Document 4 describes the influence of a thrombin mutant, in which serine in the active center is replaced with alanine, on leukocytes. Non-patent Document 5 describes a thrombin mutant in which glycine at position 203 in the B chain is replaced with alanine, a thrombin mutant in which serine in the active center is replaced with alanine or threonine, a thrombin mutant in which histidine in the active center is replaced with asparagine, and a thrombin mutant in which aspartic acid in the active center is replaced with asparagine. However, the thrombin mutants described in Non-patent Documents 4 and 5 do not have sufficient efficiency as an antithrombotic agent or anti-inflammatory agent because of the following reasons: they still have residual enzymatic activity (thrombin substrate-cleaving activity) at a level which cannot be detected by the measurement method described in each of the documents; a thrombin substrate-binding ability thereof is remarkably impaired; or the thrombin mutants have high binding ability to Fbgn which is present in a large amount in blood.

Patent Document 1 and Non-patent Documents 6, 7, and 8 describe thrombin mutants each having an enzymatic activity (thrombin substrate-cleaving activity) and an anti-blood coagulation effect obtained by replacing an amino acid thereof Those thrombin mutants are each a thrombin mutant in which a binding ability to thrombomodulin (hereinafter, may be referred to as "TM") is maintained or enhanced, a fibrinogen-cleaving ability is remarkably decreased, and an antithrombotic effect is exhibited by binding specifically to TM and activating protein C.

Patent Document 2 discloses a prothrombin derivative which has an amino acid substitution in the active center and is intended to be used for neutralizing an anticoagulation activity of a hirudin C-terminal peptide when problems such as bleeding occurs by administration of the hirudin C-terminal peptide as an antithrombotic agent to a patient.

Patent Documents 3 and 4 describe that a thrombin mutant in which serine in the active center was replaced with alanine and a thrombin mutant in which serine in the active center was replaced with alanine and aspartic acid in the active center was replaced with asparagine inhibited the stimulation of a thrombin receptor by thrombin in a washed platelet suspension.

Patent Document 5 describes various kinds of thrombin mutants which: have lost a substrate-cleaving activity; have decreased affinity to fibrinogen, heparin, and thrombomodulin; and have high antithrombotic ability, as a result of amino acid substitutions in the active center and other sites.

However, the thrombin mutant reported in Patent Document 5 has a little affinity to a heparin-like substance (heparan sulfate), thrombomodulin, and integrin, which are present in a vascular wall, and hence the mutant binds to the vascular wall or the like, a circulating volume thereof in the blood was insufficient, and a half life thereof was short as a result of endocytosis by a vascular endothelium. Thus, there has remained to be improved.

Then, there has been demand for thrombin mutants which have lower affinities to heparin, thrombomodulin, and integlin, and have improved antithrombotic ability.

Patent Document 1: WO 95/13385
Patent Document 2: WO 96/41868
Patent Document 3: WO 92/14750
Patent Document 4: U.S. Pat. No. 5,256,766
Patent Document 5: WO 2005/089070
Non-patent Document 1: J. Biol. Chem. 261 (1986) 15928-15933
Non-patent Document 2: Japanese Journal of Thrombosis and Hemostasis, Vol. 10, Nos. 2 and 3 (1999)
Non-patent Document 3: Voet, Biochemistry, Volume 1, 1996, p. 331-340, TOKYO KAGAKU DOZIN, CO., LTD.
Non-patent Document 4: Experimental cell research, 219, 650-656 (1995)
Non-patent Document 5: Biochimica et BiophysciaActa, 1451 (1999) 173-186
Non-patent Document 6: J. Biol. Chem, Vol. 275, 39827-39830
Non-patent Document 7: J. Biol. Chem, Vol. 279, 26387-26394
Non-patent Document 8: J. Biol. Chem, Vol. 277, 27581-27584

DISCLOSURE OF THE INVENTION

An object of the present invention is to provide a thrombin mutant which has decreased affinity to heparin, thrombomodulin, or integrin while improving or not impairing an antithrombotic action.

The inventors of the present invention have extensively studied to solve the above object. As a result, the inventors have found that an inactivated thrombin mutant having a decreased affinity to heparin and an improved APTT-prolonging effect can be obtained by replacing at least serine at position 205 among the amino acids in the active center of thrombin B chain and arginine at position 89 in the B chain with other amino acids. Further, the inventors have found that a thrombin mutant having decreased affinity to thrombomodulin and maintaining the APTT-prolonging effect and a PAR1 activation-inhibiting ability can be obtained by replacing with other amino acids threonine at position 69 and/or serine at position 22 together with at least the serine at position 205 in the B chain among amino acids in the active center of thrombin B chain. Further, the inventors have found that the binding ability to integrin can be decreased without impairing the APTT-prolonging effect by replacing, with other amino acids, at least the serine at position 205 among amino acids in the active center of thrombin B chain and the alanine at position 200 in the B chain. Further, the inventors have found that higher APTT-prolonging effect can be obtained by replacing at least serine at position 205 among amino acids in the active center of thrombin B chain with another amino acid and lysine at position 65 with threonine. Thus, the present invention has been completed.

That is, the present invention is as follows.

(1) A thrombin mutant, a B chain of which has a replacement of at least serine at position 205 among the amino acids of the active center of the B chain with another amino acid, and at least one replacement selected from the group consisting of (I) to (IV):

(I) replacement of arginine at position 89 in the B chain with another amino acid;

(II) replacement of threonine at position 69 or serine at position 22 in the B chain with another amino acid;

(III) replacement of alanine at position 200 in the B chain with another amino acid; and (IV) replacement of lysine at position 65 in the B chain with threonine.

(2) The thrombin mutant according to (1), wherein the amino acid that replaces the threonine at position 69 and the serine at position 22 in the B chain is an amino acid having two or more alkyl groups at a side chain.

(3) A thrombin mutant, a B chain of which has a replacement of at least serine at position 205 among amino acids in an active center of a thrombin B chain with another amino acid, and a replacement of lysine at position 65 in the B chain with threonine.

(4) The thrombin mutant according to any one of (1) to (3), wherein at least serine at position 205 and histidine at position 43 among amino acids in the active center of thrombin B chain are replaced with another amino acid.

(5) A polynucleotide, which encodes the thrombin mutant according to any one of (1) to (4).

(6) A recombinant vector, which comprises the polynucleotide according to (5).

(7) A transformant, which is introduced with the recombinant vector according to (6).

(8) A method of producing a thrombin mutant, comprising: culturing the transformant according to (7) to produce the thrombin mutant according to any one of (1) to (4).

(9) A pharmaceutical composition, comprising the thrombin mutant according to any one of (1) to (4).

(10) A pharmaceutical composition according to (9), which is an antithrombotic agent.

BEST MODE FOR CARRYING OUT THE INVENTION

Hereinafter, the present invention is described in detail.

The thrombin mutant of the first type of the present invention is a thrombin mutant in which at least serine at position 205 (B chain 205: corresponding to the serine at position 254 in SEQ ID NO: 2) among amino acids in the active center of thrombin B chain, and arginine at position 89 in the B chain (B chain 89: corresponding to arginine at position 138 in SEQ ID NO: 2) are each replaced with another amino acid.

In this description, as an amino acid which is in the active center of thrombin B chain, in addition to the serine at position 205, there are exemplified glycine at position 203 (B chain 203: corresponding to glycine at position 252 in SEQ ID NO: 2), aspartic acid at position 99 (B chain 99: corresponding to aspartic acid at position 148 in SEQ ID NO: 2), and histidine at position 43 (B chain 43: corresponding to histidine at position 92 in SEQ ID NO: 2). In the amino acid in the active center of the thrombin mutant of the present invention, one or more amino acids among the glycine at position 203, the aspartic acid at position 99, and the histidine at position 43, in addition to the serine at position 205, may be replaced with other amino acids. Among the amino acids in the active center of the B chain of the thrombin mutant of the present invention, it is preferable that the serine at position 205 and the histidine at position 43 are replaced with other amino acids. That is, a preferable example of the thrombin mutant of the first type of the present invention is a thrombin mutant in which the serine at position 205 in the B chain, the histidine at position 43 in the B chain, and the arginine at position 89 in the B chain are replaced with another amino acid.

One example of the amino acid sequence of the thrombin mutant which is the first type of the present invention is shown in SEQ ID NO: 6 (the B chain is represented by amino acid numbers 50 to 308).

The amino acid which replaces the arginine at position 89 in the B chain is not particularly limited as long as the amino acid decreases the affinity of the thrombin mutant to heparin, and is preferably alanine.

In the thrombin mutant of the present invention, the serine at position 205 in the B chain is preferably replaced with alanine, threonine, or glycine. Of those, the serine is particularly preferably replaced with alanine. The glycine at position 203 in the B chain is preferably replaced with any one of alanine, serine, and threonine. The aspartic acid at position 99 in the B chain is preferably replaced with asparagine. The histidine at position 43 in the B chain is preferably replaced with alanine, serine, or asparagine. The histidine is more preferably replaced with alanine.

In the thrombin mutant of the first type, the affinity to heparin is decreased and the APTT-prolonging effect is improved as compared to that prior to the amino acid substitution.

The affinity to heparin can be confirmed by a binding assay using a heparin column or the like (WO 2005/089070).

Prolongation of activated partial thromboplastin time (APTT) can be confirmed by measuring the APTT of a plasma to which the mutant is added according to a general APTT measurement method and comparing the result with a control value.

A thrombin mutant of the second type of the present invention is a thrombin mutant in which at least the serine at position 205 among amino acids in the active center of thrombin B chain, and threonine at position 69 in the chain B (B chain 69: corresponding to threonine at position 118 in SEQ ID NO: 2), and/or serine at position 22 in the B chain (B chain 22: corresponding to serine at position 71 in SEQ ID NO: 2) are replaced with another amino acid.

This thrombin mutant includes (i) a thrombin mutant in which the threonine at position 69 in the B chain and the serine at position 205 in the B chain are replaced with another amino acid, (ii) a thrombin mutant in which the serine at position 22 in the B chain and the serine at position 205 in the B chain are replaced with another amino acid, and (iii) a thrombin mutant in which the threonine at position 69 in the B chain, the serine at position 22 in the B chain, and the serine at position 205 in the B chain are replaced with another amino acid.

In the combinations of the items (i) to (iii), one or more amino acids among the glycine at position 203, the aspartic acid at position 99, and the histidine at position 43 may also be replaced with other amino acids. In the combinations of the items (i) to (iii), it is preferable that the histidine at position 43 is also replaced with another amino acid.

One example of the amino acid sequence in the thrombin mutant which is the second type of the present invention is shown in SEQ ID NO: 12 (the B chain is represented by amino acid numbers 50 to 308).

The threonine at position 69 in the B chain is replaced preferably with an amino acid having two or more alkyl groups at the side chain (for example, glutamine, arginine, leucine, methionine, lysine, isoleucine, glutamic acid, or valine) and particularly preferably replaced with glutamine.

The serine at position 22 in the B chain is also replaced with an amino acid having two or more alkyl groups at the side chain (for example, glutamine, arginine, leucine, methionine, lysine, isoleucine, glutamic acid, or valine) and particularly preferably replaced with glutamine.

In the thrombin mutant of the second type, the affinity to thrombomodulin is decreased, and the thrombin mutant has almost the same APTT-prolonging effect and PAR1 activation-inhibiting ability as those prior to the substitution of the threonine at position 69 in the B chain or the substitution of the serine at position 22.

The decrease in the affinity to thrombomodulin can be confirmed by a binding assay using a thrombin-binding cuvette as described below.

A thrombin mutant of the third type of the present invention is a thrombin mutant in which at least the serine at position 205 among amino acids in the active center of thrombin B chain and alanine at position 200 in the B chain (B chain 200: corresponding to alanine at position 249 in SEQ ID NO: 2) are replaced with another amino acid.

In addition to the alanine at position 200 and the serine at position 205 in the B chain, one or more amino acids among the glycine at position 203, the aspartic acid at position 99, and the histidine at position 43 may be also replaced with another amino acid. It is preferable that, in addition to the alanine at position 200 and the serine at position 205 in the B chain, the histidine at position 43 is replaced with another amino acid.

One example of the amino acid sequence of the thrombin mutant which is the third type of the present invention is shown in SEQ ID NO: 16 (the B chain is represented by amino acid numbers 50 to 308).

The amino acid which replaces the alanine at position 200 in the B chain is not particularly limited as long as the amino acid decreases the affinity of the thrombin mutant to integrin, and is preferably serine.

In the thrombin mutant of the third type, the affinity to integrin is decreased and the APTT-prolonging effect is maintained as that prior to the amino acid substitution.

In the thrombin mutants of the first to third types of the present invention, lysine at position 65 in the B chain (B chain 65: corresponding to lysine at position 114 in SEQ ID NO: 2) may be replaced with another amino acid. As the amino acid which replaces the lysine at position 65 in the B chain, alanine and threonine are exemplified, and threonine is more preferred.

A thrombin mutant of the fourth type of the present invention is a thrombin mutant in which at least the serine at position 205 among the amino acids in the active center of thrombin B chain is replaced with another amino acid and the lysine at position 65 in the B chain (B chain 65: corresponding to lysine at position 114 in SEQ ID NO: 2) is replaced with threonine.

In addition to the lysine at position 65 and the serine at position 205 in the B chain, one or more amino acids among the glycine at position 203, the aspartic acid at position 99, and the histidine at position 43 may be replaced with other amino acids. It is preferable that, in addition to the lysine at position 65 and the serine at position 205 in the B chain, the histidine at position 43 is replaced.

One example of the amino acid sequence of the thrombin mutant which is the fourth type of the present invention is shown in SEQ ID NO: 14 (amino acid numbers 50 to 308 show the B chain).

In the thrombin mutant of the fourth type, the APTT-prolonging effect is improved as compared to the case where the lysine at position 65 in the B chain is replaced with alanine.

It should be noted that, in this description, the serine at position 205 in the B chain, the arginine at position 89 in the B chain, the threonine at position 69 in the B chain, the serine at position 22 in the B chain, the alanine at position 200 in the B chain, the lysine at position 65 in the B chain, and the like indicate the amino acids at the position counted from the amino acid at position 1 of the B chain (for example, isoleucine at the amino acid number 50 in SEQ ID NO: 2). It should be noted that the positions of the above-mentioned replaced amino acids may be changed by deletion, insertion, or addition of an amino acid or the like. For example, if an amino acid residue is inserted in the N-terminal part, the position 205 which is the original position of serine shifts to the position 206. However, the serine corresponding to the serine at position 205 is also referred to as serine at position 205 in the present invention.

In the thrombin mutant of the present invention, the replacements of amino acids in the first to fourth types may be combined.

Further, the thrombin mutant of the present invention may be a thrombin mutant having an amino acid sequence in which one or several amino acids are replaced, deleted, inserted, or added in the B chain (amino acid numbers 50 to 308 in SEQ ID NO: 2) in addition to the particular amino acid as described above, as long as the effect of the present invention is not impaired. It should be noted that the term "one or several" means 1 to 20, preferably 1 to 10, and more preferably 1 to 5. Further, the thrombin mutant of the present invention may be a thrombin mutant having an amino acid sequence in which one or several amino acids are replaced, deleted, inserted, or added also in the A chain (amino acid numbers 1 to 49 in SEQ ID NO: 2). It should be noted that the term "one or several" means 1 to 10, preferably 1 to 5, and more preferably 1 to 3 in this case.

It is preferable that the amino acid sequence of the thrombin mutant of the present invention is at least 80% identical to the amino acid sequence of SEQ ID NO: 2, more preferably at least 90%, further more preferably at least 95%, and particularly preferably at least 98% identical to the amino acid sequence of SEQ ID NO: 2.

A thrombin mutant to be used in the present invention is a thrombin mutant which comprises an A chain and a B chain, and in which the specific amino acids in the B chain are replaced. The thrombin mutant to be used in the present invention is not particularly limited as long as it can form a tertiary structure in which the A chain and the B chain are cross-linked to each other through an S—S bond in vivo. The A chain and the B chain are each produced by processing of a thrombin precursor protein, so the thrombin mutant of the present invention may be administered to a living body in a form of a precursor protein such as prethrombin or prothrombin so as to be processed in the living body to form the tertiary structure. Meanwhile, the A chain and the B chain may be separately produced by gene recombination, chemical synthesis, or the like, and then the S—S bonds between them are allowed to be formed in vitro, or they may be separately administered so as to form the tertiary structure, in which the A chain and the B chain are cross-linked to each other through the S—S bonds in vivo.

Here, the A chain is a region corresponding to amino acid numbers 1 to 49 in SEQ ID NO: 2 in the case of human wild-type thrombin. The B chain is a region corresponding to amino acid numbers 50 to 308 in SEQ ID NO: 2 in the case of human wild-type thrombin.

In human thrombin, 13 amino acid residues at an N-terminal of the A chain are cleaved out therefrom by autolysis. Therefore, the A chain may be a sequence in which the 13 amino acid residues (e.g., amino acid numbers 1 to 13 in SEQ ID NO: 2) at the N terminal have been deleted. Further, thrombin precursor proteins such as prothrombin and prethrombin each of which can form the tertiary structure as described above in vivo are also encompassed in the thrombin mutant of the present invention. The amino acid sequence of human wild-type prothrombin is disclosed in the database of Swissprot with an accession number of P00734.

The thrombin mutants of the present invention may be administered into a living body in a form of prothrombin. In this case, the thrombin mutant is activated to form thrombin having an antithrombotic effect at a thrombotic site, and an antithrombotic effect is exerted at the area where a thrombus is formed, thereby attaining a more site-directed antithrombotic effect in vivo.

The thrombin mutant of the present invention is obtained by, for example, cloning a wild-type thrombin gene (for example, SEQ ID NO: 3) by PCR or the like, introducing an intended mutation by a site-directed mutagenesis and the like to produce a DNA coding for each mutant, inserting the DNA into a vector or the like, and expressing the DNA in a mammalian cell such as a Chinese hamster ovary (CHO) cell. The DNA may be a DNA coding for both an A chain and the B chain as described above or each chain may be expressed separately. The site-directed mutagenesis method is not particularly limited. For example, QuikChange Site-Directed Mutagenesis Kit (manufactured by Stratagene) or the like may be used. In addition, the thrombin mutant can be obtained by a chemical synthesis.

As a polynucleotide coding for the thrombin mutant of the present invention, there are exemplified nucleotide sequences of SEQ ID NOS: 5, 11, 13, and 15. However, the polynucleotide is not particularly limited as long as it codes for the thrombin mutant of the present invention. It should be noted that the polynucleotide may be a polynucleotide which hybridizes with a nucleotide sequence complementary to SEQ ID NOS: 5, 11, 13, and 15 under stringent conditions, and encodes a thrombin mutant that has at least the above-mentioned specific mutation, and has a desirable effect. Here, the stringent conditions are such that washing is performed at 65° C. in a salt concentration corresponding to 0.1×SSC and 0.1% SDS once or preferably twice or three times.

By combining the thrombin mutant of the present invention with a pharmaceutically acceptable carrier, the thrombin mutant can be formulated into a pharmaceutical composition. The pharmaceutically acceptable carrier is not particularly limited and a solvent for an injection, a stabilizer, a diluent, a surfactant, or the like, each of which is generally used for pharmaceuticals, can be used. The form of dosage unit for the pharmaceutical composition of the present invention is not particularly limited and can be selected appropriately according to the therapeutic purpose. For example, an injection or the like is exemplified. The dosage of the pharmaceutical composition of the present invention is selected appropriately according to symptoms.

Examples of the application of the pharmaceutical composition include a therapeutic agent for thrombosis, an anti-inflammatory agent, a platelet aggregation-inhibiting agent, a platelet-aggregation-inhibiting agent, and a thrombin receptor activation-inhibiting agent.

EXAMPLES

Experimental Example 1

(1) Expression of a Human Wild-Type Thrombin

A DNA (SEQ ID NO: 3) containing an A chain and a B chain of human wild-type thrombin was inserted into a vector to transfect a CHO cell, to thereby obtain a prethrombin producing cell.

It should be noted that the sequence of the human wild-type prethrombin shown in SEQ ID NO: 4 includes a signal sequence of amino acid numbers 1 to 43, an A chain of amino acid numbers 44 to 92, and a B chain of amino acid numbers 93 to 351.

The prethrombin producing cell was cultured in 2 liters of a CD-CHO medium for 10 days. 2 liters of the obtained culture solution of the prethrombin producing cell was subjected to dialysis against 20 liters of 10 mM PIPES buffer solution (pH 7) at 4° C. twice for 6 hours each. Then, the dialysate was added to 500 ml of CM cellulofine (Chisso Corporation) and washed with 1 liter of 10 mM PIPES buffer solution (pH 7). Next, elution was performed with a linear concentration gradient from 0 to 1 M NaCl in 10 mM PIPES buffer solution (pH 7). The eluate was divided into fractions of 25 ml each, and each of the fractions was subjected to Western blotting by using an anti-human thrombin polyclonal antibody (Cosmo Bio Co., Ltd.), to thereby confirm that the human wild-type thrombin was eluted at about 0.5 M.

(2) Purification of Human Wild-Type Thrombin

Next, 98 ml of a solution containing the ecarin-activated thrombin, which is the rest of the thrombin used in the hirudin C-terminal peptide binding experiment, was added to 200 ml of a sulfated cellulofine column (Chisso Corporation) which had been equilibrated with 50 mM Tris-HCl buffer (pH 8) containing 0.1 M NaCl. The column was washed with 200 ml of the buffer, and then elution was performed with 50 mM Tris-HCl buffer (pH 8) containing 1 M NaCl. The eluate was subjected to dialysis against 50 mM Tris-HCl buffer (pH 8). The dialysate was added to 30 ml of a hirudin C-terminal peptide column (200 mg of the hirudin C-terminal peptide immobilized to the NHS-activated cellulofine (Chisso Corporation)) which had been equilibrated with the buffer. The hirudin C-terminal peptide column (WO 2005/089070) was washed with 150 ml of 50 mM Tris-HCl buffer and then subjected to elution with 50 mM Tris-HCl buffer (pH 8) containing 1 M NaCl and 4 M guanidine hydrochloride, to thereby obtain about 5 mg of human wild-type thrombin having hirudin-binding ability, which looked almost-purified on SDS-PAGE.

(3) APTT Measurement

The measurement of APTT was conducted by the following method otherwise not specified in the Examples.

A standard plasma (SYSMEX INTERNATIONAL REAGENTS CO., LTD.) and a test sample are mixed and an APTT reagent (SYSMEX INTERNATIONAL REAGENTS CO., LTD.) in amount of 25% with respect to the total amount is added thereto, followed by incubation at 37° C. for 5 minutes. After 5 minutes, 0.1 M CaCl$_2$ is added so as to have the concentration of 8 mM and the time from the addition of calcium to coagulation is measured.

(4) Method of Confirming a Heparin-Binding Ability F 5 ml of the human wild-type thrombin or each of the thrombin mutants was added to HI-TRAP HEPARIN column (Amersham Pharmacia) equilibrated with 50 mM NaHCO$_3$/50 mM NaCl solution. Then, after the column was washed with 15 ml of 50 mM NaHCO$_3$/0.1 M NaCl solution, elution was performed with a gradient from 0% B buffer to 100% B buffer at a flow rate of 0.5 ml/min for 100 minutes by using a buffer A (50 mM NaHCO$_3$/0.1 M NaCl) and a buffer B (50 mM NaHCO$_3$/1 M NaCl).

Example 1

(1) Expression of the thrombin mutant (hereinafter referred to as 89A65A43A205A thrombin) in which arginine at position 89 in B chain is replaced with alanine, lysine at position 65 in B chain is replaced with alanine, histidine at position 43 in B chain is replaced with alanine, and serine at position 205 in B chain is replaced with alanine A DNA coding for 89A65A43A205A thrombin was synthesized by a PCR method using a mutation-introduced primer corresponding to each mutation. The nucleotide sequence of the DNA coding for the 89A65A43A205A thrombin is shown in SEQ ID NO: 5.

The 89A65A43A205A thrombin was expressed by the method described in the section (1) in Experimental Example 1. The 89A65A43A205A thrombin was purified with a sulfated cellulofine column and a hirudin C-terminal peptide column according to the method in the section (2) of Experimental Example 1. Then, about 5 mg of 89A65A43A205A thrombin, which looked almost-purified on SDS-PAGE, was obtained. The binding ability to a heparin gel was measured, and the 89A65A43A205A thrombin was eluted with about 0.3 M NaCl (wild-type human thrombin is eluted with about 0.5 M NaCl).

(2) Measurement of APTT of 89A65A43A205A Thrombin

100 µl of 50 µg/ml 89A65A43A205A thrombin (diluted in PBS (137 mM NaCl, 2.68 mM KCl, 8.1 mM Na$_2$HPO$_4$, 1.47 mM KH$_2$PO$_4$ (pH7.4))) and 100 µl of a standard plasma (SYSMEX INTERNATIONAL REAGENTS CO., LTD.) were mixed, followed by measurement of APTT. When APTT was measured by using, as a control, a standard plasma added with only PBS in the same way, the APTT was 46 seconds. The APTT of the 89A65A43A205A thrombin was 121 seconds, which was 2.63 times as long as the control.

Comparative Example 1

(1) Expression of the thrombin mutant (hereinafter referred to as 43A205A thrombin) in which histidine at position 43 in B chain is replaced with alanine, and serine at position 205 in B chain is replaced with alanine A DNA coding for 43A205A thrombin was synthesized by a PCR method using a mutation-introduced primer corresponding to each mutation. The nucleotide sequence of the DNA coding for the 43A205A thrombin is shown in SEQ ID NO: 7.

The 43A205A thrombin was expressed by the method in the section (1) of Experimental Example 1. The 43A205A thrombin was purified with a sulfated cellulofine column and a hirudin C-terminal peptide column according to the method in the section (2) of Experimental Example 1. Then, about 5 mg of 43A205A thrombin, which looked almost-purified on SDS-PAGE, was obtained. The binding ability to a heparin gel was measured according to the method in the section (4) of Experimental Example 1, and the 43A205A thrombin was eluted with about 0.5 M NaCl as in the case of the wild-type human thrombin.

(2) Measurement of APTT of 43A205A Thrombin

100 µl of 50 µg/ml 43A205A thrombin (diluted in PBS (137 mM NaCl, 2.68 mM KCl, 8.1 mM Na$_2$HPO$_4$, 1.47 mM KH$_2$PO$_4$ (pH7.4))) and 100 µl of a standard plasma (SYSMEX INTERNATIONAL REAGENTS CO., LTD.) were mixed, followed by measurement of APTT. When APTT was measured by using, as a control, a standard plasma added with only PBS in the same way, the APTT was 43 seconds. The APTT of the 43A205A thrombin was 75.5 seconds, which was 1.76 times as long as the control.

Comparative Example 2

(1) Expression of the thrombin mutant (hereinafter referred to as 65A43A205A thrombin) in which lysine at position 65 in B chain is replaced with alanine, histidine at position 43 in B chain is replaced with alanine, and serine at position 205 in B chain is replaced with alanine A DNA coding for 65A43A205A thrombin was synthesized by a PCR method using a mutation-introduced primer corresponding to each mutation. The nucleotide sequence of the DNA coding for the 65A43A205A thrombin is shown in SEQ ID NO: 9.

The 65A43A205A thrombin was expressed by the method in the section (1) of Experimental Example 1. The 65A43A205A thrombin was purified with a sulfated cellulofine column and a hirudin C-terminal peptide column according to the method in the section (2) of Experimental Example 1. Then, about 5 mg of 65A43A205A thrombin, which looked almost-purified on SDS-PAGE, was obtained. The binding ability to a heparin gel was measured, and the 65A43A205A thrombin was eluted with about 0.5 M NaCl as in the case of the wild-type human thrombin.

(2) Measurement of APTT of 65A43A205A Thrombin

100 µl of 50 µg/ml 65A43A205A thrombin (diluted in PBS (137 mM NaCl, 2.68 mM KCl, 8.1 mM Na$_2$HPO$_4$, 1.47 mM KH$_2$PO$_4$ (pH7.4))) and 100 µl of a standard plasma (SYSMEX INTERNATIONAL REAGENTS CO., LTD.) were mixed, followed by measurement of APTT. When APTT was measured by using, as a control, a standard plasma added with only PBS in the same way, the APTT was 44.5 seconds. The APTT of the 65A43A205A thrombin was 105.5 seconds, which was 2.37 times as long as the control.

It was found that, as a result of the substitution of the arginine at position 89, a thrombin mutant having decreased affinity to heparin and improved APTT-prolonging effect was obtained.

Example 2

(1) Expression of the thrombin mutant (hereinafter referred to as 69Q65A43A205A thrombin) in which threonine at position 69 in B chain is replaced with glutamine, lysine at position 65 in B chain is replaced with alanine, histidine at position 43 in B chain is replaced with alanine, and serine at position 205 in B chain is replaced with alanine A DNA coding for 69Q65A43A205A thrombin was synthesized by a PCR method using a mutation-introduced primer corresponding to each mutation. The nucleotide sequence of the DNA coding for the 69Q65A43A205A thrombin is shown in SEQ ID NO: 11.

The 69Q65A43A205A thrombin was expressed by the method in the section (1) of Experimental Example 1. The 69Q65A43A205A thrombin was purified with a sulfated cellulofine column and a hirudin C-terminal peptide column according to the method in the section (2) of Experimental Example 1. Then, about 5 mg of 69Q65A43A205A thrombin, which looked almost-purified on SDS-PAGE, was obtained.

The binding ability to a heparin gel was measured according to the method in the section (4) of Experimental Example 1, and the 69Q65A43A205A thrombin was eluted with about 0.5 M NaCl as in the case of the wild-type human thrombin.

(2) Measurement of APTT of 69Q65A43A205A Thrombin

100 μl of 50 μg/ml 69Q65A43A205A thrombin (diluted in PBS (137 mM NaCl, 2.68 mM KCl, 8.1 mM $Na_2HPO_4$, 1.47 mM $KH_2PO_4$ (pH7.4))) and 100 μl of a standard plasma (SYSMEX INTERNATIONAL REAGENTS CO., LTD.) were mixed, followed by measurement of APTT. When APTT was measured by using, as a control, a standard plasma added with only PBS in the same way, the APTT was 45 seconds. The APTT of the 69Q65A43A205A thrombin was 105.5 seconds which was almost as long as that of the 65A43A205A thrombin.

(3) Confirmation of Binding Specificity of 69Q65A43A205A Thrombin to TM 10 mM phosphate buffer (pH 7) solution containing 0.1 mg/ml 69Q65A43A205A thrombin and 10 mM phosphate buffer (pH 7) containing 0.1 mg/ml 65A43A205A thrombin were each added to an NHS-activated CM dextran cuvette (Nissei Sangyo Co., Ltd.). Then, the resultant were stirred at 25° C. for 10 minutes, thereby each sample (thrombin mutant) was immobilized to the NHS-activated CM dextran cuvette. As a result, a 69Q65A43A205A thrombin-immobilized cuvette and a 65A43A205A thrombin-immobilized cuvette were obtained. In the 69Q65A43A205A thrombin cuvette and the 65A43A205A thrombin cuvette, a protein of about 1,365 arc and a protein of about 1,800 arc were immobilized, respectively. Subsequently, 0.2 ml of 1 M ethanol amine (pH 8) was added to each ceuvette, to carry out a blocking treatment.

Both cuvettes were washed with 50 mM phosphate buffer, 2 M NaCl, and 30 mM benzamidine (pH 7.4). After the recovery, 100 μl of 50 nM soluble TM solution (COSMO BIO. co., ltd.) (TM dissolved in a solution containing 50 mM phosphate buffer, 0.15 M NaCl (pH7.4)) were added to each of the 69Q65A43A205A thrombin-immobilized cuvette and the 65A43A205A thrombin-immobilized cuvette. 10 minutes later, a TM of about 8 arc sec was adsorbed in the 69Q65A43A205A thrombin-immobilized cuvette and a TM of about 18 arc sec was adsorbed in the 65A43A205A thrombin-immobilized cuvette. (When the immobilized amount was set to 1000 arc sec, the TM of 5.8 arc sec and the TM of 10 arc sec were adsorbed in the 69Q65A43A205A thrombin-immobilized cuvette and the 65A43A205A thrombin-immobilized cuvette, respectively). It was found that, by replacing the serine at position 69 with glutamine, the TM-binding ability was further decreased while the APTT-prolonging effect was maintained.

Example 3

(1) Expression of the thrombin mutant (hereinafter referred to as 65T43A205A thrombin) in which lysine at position 65 in B chain is replaced with threonine, histidine at position 43 in B chain is replaced with alanine, and serine at position 205 in B chain is replaced with alanine A DNA coding for 65T43A205A thrombin was synthesized by a PCR method using a mutation-introduced primer corresponding to each mutation. The nucleotide sequence of the DNA coding for the 65T43A205A thrombin is shown in SEQ ID NO: 13.

The 65T43A205A thrombin was expressed by the method in the section (1) of Experimental Example 1. The 65T43A205A thrombin was purified with a sulfated cellulofine column and a hirudin C-terminal peptide column according to the method in the section (2) of Experimental Example 1. Then, about 5 mg of 65T43A205A thrombin, which looked almost-purified on SDS-PAGE, was obtained. The binding ability to a heparin gel was measured, and the 65T43A205A thrombin was eluted with about 0.5 M NaCl as in the case of the wild-type human thrombin.

(2) Measurement of APTT of 65T43A205A Thrombin

100 μl of 50 μg/ml 65T43A205A thrombin (diluted in PBS (137 mM NaCl, 2.68 mM KCl, 8.1 mM $Na_2HPO_4$, 1.47 mM $KH_2PO_4$ (pH7.4))) and 100 μl of a standard plasma (SYSMEX INTERNATIONAL REAGENTS CO., LTD.) were mixed, followed by measurement of APTT. When APTT was measured by using, as a control, a standard plasma added with only PBS, the APTT was 45 seconds. The APTT of the 65T43A205A thrombin was 120 seconds, which was 2.67 times as long as that of the control. The thrombin in which the lysine at position 65 was replaced with threonine (65T43A205A thrombin) prolonged APTT more effectively than the thrombin in which the lysine at position 65 was replaced with alanine (65A43A205A thrombin).

Example 4

(1) Expression of the thrombin mutant (hereinafter referred to as 200S65A43A205A thrombin) in which alanine at position 200 in B chain is replaced with serine, lysine at position 65 in B chain is replaced with alanine, histidine at position 43 in B chain is replaced with alanine, and serine at position 205 in B chain is replaced with alanine A DNA coding for 200S65A43A205A thrombin was synthesized by a PCR method using a mutation-introduced primer corresponding to each mutation. The nucleotide sequence of the DNA coding for the 200S65A43A205A thrombin is shown in SEQ ID NO: 15.

The 200S65A43A205A thrombin was expressed by the method in the section (1) of Experimental Example 1. The 200S65A43A205A thrombin was purified with a sulfated cellulofine column and a hirudin C-terminal peptide column according to the method in the section (2) of Experimental Example 1. Then, about 5 mg of 200S65A43A205A thrombin, which looked almost-purified on SDS-PAGE, was obtained. The binding ability to a heparin gel was measured, and the 200S65A43A205A thrombin was eluted with about 0.5 M NaCl as in the case of the wild-type human thrombin.

(2) Measurement of APTT of 200S65A43A205A Thrombin

100 μl of 50 μg/ml 200S65A43A205A thrombin (diluted in PBS (137 mM NaCl, 2.68 mM KCl, 8.1 mM $Na_2HPO_4$, 1.47 mM $KH_2PO_4$ (pH7.4))) and 100 μl of a standard plasma (SYSMEX INTERNATIONAL REAGENTS CO., LTD.) were mixed, followed by measurement of APTT. When APTT was measured by using, as a control, a standard plasma added with only PBS, the APTT was 44 seconds. The APTT of the 200S65A43A205A thrombin was 104 seconds, which was 2.36 times as long as the control. It was found that 200S65A43A205A thrombin showed the same APTT-prolonging effect as that of the 65A43A205A thrombin.

A mutant which has a mutation in a thrombin-specific integrin-binding sequence (RGDA sequence) and maintains APTT-prolonging effect was obtained by replacing alanine at position 200 in the B chain with serine.

Comparative Example 3

(1) Expression of the thrombin mutant (hereinafter referred to as 197A65A43A205A thrombin) in which arginine at position 197 in B chain is replaced with alanine, lysine at position 65 in B chain is replaced with alanine, histidine at position 43 in B chain with replaced with alanine, and serine at position 205 in B chain with replaced with alanine A DNA coding for 197A65A43A205A thrombin was synthesized by a PCR method using a mutation-introduced primer corresponding to each mutation. The nucleotide sequence of the DNA coding for the 197A65A43A205A thrombin is shown in SEQ ID NO: 17.

The 197A65A43A205A thrombin was expressed by the method in the section (1) of Experimental Example 1. The 197A65A43A205A thrombin was purified by sulfated cellulofine according to the method in the section (2) of Experimental Example 1. The 197A65A43A205A thrombin did not bind to the hirudin C-terminal peptide column. About 5 mg of 197A65A43A205A thrombin, which looked almost-purified on SDS-PAGE, was obtained.

(2) Measurement of APTT of 197A65A43A205A Thrombin

100 μl of 50 μg/ml 197A65A43A205A thrombin (PBS; 137 mM NaCl, 2.68 mM KCl, 8.1 mM $Na_2HPO_4$, 1.47 mM $KH_2PO_4$ (pH7.4)) and 100 μl of a standard plasma (SYSMEX INTERNATIONAL REAGENTS CO., LTD.) were mixed, followed by measurement of APTT. When APTT was measured by using, as a control, a standard plasma added with only PBS, the APTT was 46 seconds. The APTT of the 197A65A43A205A thrombin was 83 seconds, which was 1.8 as long as the control. The APTT-prolonging effect of the 197A65A43A205A thrombin was lower as compared with that of the 65A43A205A thrombin.

INDUSTRIAL APPLICABILITY

The thrombin mutant of the present invention can be used effectively in a therapy for thrombosis without side effect because the affinity thereof to a heparin-like substance (heparan sulfate), thrombomodulin, and/or integrin, which are present in the vascular wall, is decreased remarkably and the thrombin mutant has high antithrombotic ability.

The invention claimed is:

1. A thrombin mutant comprising:

an isolated B chain that comprises a replacement of a serine at position 205 and a threonine at position 69 in the isolated B chain with another amino acid, wherein the isolated B chain is counted from amino acid number 50 of SEQ ID NO:2, and wherein the thrombin mutant comprises an activated partial thromboplastin time (APTT) prolonging effect.

2. The thrombin mutant of claim 1, wherein the amino acid that replaces the threonine at position 69 in the isolated B chain of SEQ ID NO:2 is an amino acid having at least two alkyl groups as a side chain.

3. The thrombin mutant of claim 1, further comprising a replacement of a lysine at position 65 in the isolated B chain of SEQ ID NO:2 with alanine or threonine.

4. The thrombin mutant of claim 1, further comprising a replacement of a histidine at position 43 in the isolated B chain of SEQ ID NO:2 with another amino acid.

5. The thrombin mutant of claim 2, further comprising a replacement of a histidine at position 43 in the isolated B chain of SEQ ID NO:2 with another amino acid.

6. The thrombin mutant of claim 3, further comprising a replacement of a histidine at position 43 in the isolated B chain of SEQ ID NO:2 with another amino acid.

7. A pharmaceutical composition comprising the thrombin mutant of claim 1 in a pharmaceutically acceptable carrier.

8. A pharmaceutical composition comprising the thrombin mutant of claim 2 in a pharmaceutically acceptable carrier.

9. A pharmaceutical composition comprising the thrombin mutant of claim 3 in a pharmaceutically acceptable carrier.

10. A pharmaceutical composition comprising the thrombin mutant of claim 4 in a pharmaceutically acceptable carrier.

11. A pharmaceutical composition comprising the thrombin mutant of claim 5 in a pharmaceutically acceptable carrier.

12. A pharmaceutical composition comprising the thrombin mutant of claim 6 in a pharmaceutically acceptable carrier.

13. The thrombin mutant of claim 1, wherein the serine at position 205 is replaced with alanine, threonine or glycine, and the threonine at position 69 is replaced with an amino acid having at least two alkyl groups as a side chain.

14. The thrombin mutant of claim 1, wherein the serine at position 205 is replaced with alanine, threonine or glycine; the threonine at position 69 is replaced with an amino acid having at least two alkyl groups as a side chain, and further comprising a replacement of lysine at position 65 with alanine or threonine, and a replacement of histidine at position 43 with alanine, serine or arginine in the isolated B chain of SEQ ID NO:2.

15. The thrombin mutant of claim 14, wherein the serine at position 205 is replaced with alanine, the threonine at position 69 is replaced with glutamine, the lysine at position 65 is replaced with alanine and the histidine at position 43 is replaced with alanine.

16. The thrombin mutant of claim 1, further comprising a replacement of lysine at position 65 in the isolated B chain of SEQ ID NO:2 with another amino acid.

* * * * *

UNITED STATES PATENT AND TRADEMARK OFFICE
CERTIFICATE OF CORRECTION

PATENT NO. : 8,088,372 B2
APPLICATION NO. : 12/514735
DATED : January 3, 2012
INVENTOR(S) : Kazuya Hosokawa et al.

Page 1 of 1

It is certified that error appears in the above-identified patent and that said Letters Patent is hereby corrected as shown below:

Title Page, Item (73)

In the Assignees:

Please change the Assignees to:

JNC Corporation
Fujimori Kogyo Co., Ltd

Signed and Sealed this
Twenty-sixth Day of March, 2013

Teresa Stanek Rea
*Acting Director of the United States Patent and Trademark Office*

SEQUENCE LISTING

```
<160> NUMBER OF SEQ ID NOS: 18

<210> SEQ ID NO 1
<211> LENGTH: 927
<212> TYPE: DNA
<213> ORGANISM: Homo sapiens
<220> FEATURE:
<221> NAME/KEY: CDS
<222> LOCATION: (1)..(927)

<400> SEQUENCE: 1 acc gcc acc agt gag tac cag act ttc ttc aat ccg agg acc ttt ggc        48
Thr Ala Thr Ser Glu Tyr Gln Thr Phe Phe Asn Pro Arg Thr Phe Gly
1               5                   10                  15 tcg gga gag gca gac tgt ggg ctg cga cct ctg ttc gag aag aag tcg        96
Ser Gly Glu Ala Asp Cys Gly Leu Arg Pro Leu Phe Glu Lys Lys Ser
            20                  25                  30 ctg gag gac aaa acc gaa aga gag ctc ctg gaa tcc tac atc gac ggg       144
Leu Glu Asp Lys Thr Glu Arg Glu Leu Leu Glu Ser Tyr Ile Asp Gly
        35                  40                  45 cgc att gtg gag ggc tcg gat gca gag atc ggc atg tca cct tgg cag       192
Arg Ile Val Glu Gly Ser Asp Ala Glu Ile Gly Met Ser Pro Trp Gln
    50                  55                  60 gtg atg ctt ttc cgg aag agt ccc cag gag ctg ctg tgt ggg gcc agc       240
Val Met Leu Phe Arg Lys Ser Pro Gln Glu Leu Leu Cys Gly Ala Ser
65                  70                  75                  80 ctc atc agt gac cgc tgg gtc ctc acc gcc gcc cac tgc ctc ctg tac       288
Leu Ile Ser Asp Arg Trp Val Leu Thr Ala Ala His Cys Leu Leu Tyr
                85                  90                  95
```

| | | | | | | | | | | | | | | | |
|---|---|---|---|---|---|---|---|---|---|---|---|---|---|---|---|
| ccg | ccc | tgg | gac | aag | aac | ttc | acc | gag | aat | gac | ctt | ctg | gtg | cgc | att | 336 |
| Pro | Pro | Trp | Asp | Lys | Asn | Phe | Thr | Glu | Asn | Asp | Leu | Leu | Val | Arg | Ile |
| | | | 100 | | | | | 105 | | | | | 110 | | |

```
ccg ccc tgg gac aag aac ttc acc gag aat gac ctt ctg gtg cgc att        336
Pro Pro Trp Asp Lys Asn Phe Thr Glu Asn Asp Leu Leu Val Arg Ile
            100                 105                 110 ggc aag cac tcc cgc aca agg tac gag cga aac att gaa aag ata tcc        384
Gly Lys His Ser Arg Thr Arg Tyr Glu Arg Asn Ile Glu Lys Ile Ser
            115                 120                 125 atg ttg gaa aag atc tac atc cac ccc agg tac aac tgg cgg gag aac        432
Met Leu Glu Lys Ile Tyr Ile His Pro Arg Tyr Asn Trp Arg Glu Asn
130                 135                 140 ctg gac cgg gac att gcc ctg atg aag ctg aag aag cct gtt gcc ttc        480
Leu Asp Arg Asp Ile Ala Leu Met Lys Leu Lys Lys Pro Val Ala Phe
145                 150                 155                 160 agt gac tac att cac cct gtg tgt ctg ccc gac agg gag acg gca gcc        528
Ser Asp Tyr Ile His Pro Val Cys Leu Pro Asp Arg Glu Thr Ala Ala
                165                 170                 175 agc ttg ctc cag gct gga tac aag ggg cgg gtg aca ggc tgg ggc aac        576
Ser Leu Leu Gln Ala Gly Tyr Lys Gly Arg Val Thr Gly Trp Gly Asn
            180                 185                 190 ctg aag gag acg tgg aca gcc aac gtt ggt aag ggg cag ccc agt gtc        624
Leu Lys Glu Thr Trp Thr Ala Asn Val Gly Lys Gly Gln Pro Ser Val
            195                 200                 205 ctg cag gtg gtg aac ctg ccc att gtg gag cgg ccg gtc tgc aag gac        672
Leu Gln Val Val Asn Leu Pro Ile Val Glu Arg Pro Val Cys Lys Asp
210                 215                 220 tcc acc cgg atc cgc atc act gac aac atg ttc tgt gct ggt tac aag        720
Ser Thr Arg Ile Arg Ile Thr Asp Asn Met Phe Cys Ala Gly Tyr Lys
225                 230                 235                 240 cct gat gaa ggg aaa cga ggg gat gcc tgt gaa ggt gac agt ggg gga        768
Pro Asp Glu Gly Lys Arg Gly Asp Ala Cys Glu Gly Asp Ser Gly Gly
                245                 250                 255 ccc ttt gtc atg aag agc ccc ttt aac aac cgc tgg tat caa atg ggc        816
Pro Phe Val Met Lys Ser Pro Phe Asn Asn Arg Trp Tyr Gln Met Gly
            260                 265                 270 atc gtc tca tgg ggt gaa ggc tgt gac cgg gat ggg aaa tat ggc ttc        864
Ile Val Ser Trp Gly Glu Gly Cys Asp Arg Asp Gly Lys Tyr Gly Phe
            275                 280                 285 tac aca cat gtg ttc cgc ctg aag aag tgg ata cag aag gtc att gat        912
Tyr Thr His Val Phe Arg Leu Lys Lys Trp Ile Gln Lys Val Ile Asp
290                 295                 300 cag ttt gga gag tag                                                     927
Gln Phe Gly Glu
305
```

<210> SEQ ID NO 2
<211> LENGTH: 308
<212> TYPE: PRT
<213> ORGANISM: Homo sapiens

<400> SEQUENCE: 2

```
Thr Ala Thr Ser Glu Tyr Gln Thr Phe Phe Asn Pro Arg Thr Phe Gly
1               5                   10                  15

Ser Gly Glu Ala Asp Cys Gly Leu Arg Pro Leu Phe Glu Lys Lys Ser
            20                  25                  30

Leu Glu Asp Lys Thr Glu Arg Glu Leu Leu Glu Ser Tyr Ile Asp Gly
        35                  40                  45

Arg Ile Val Glu Gly Ser Asp Ala Glu Ile Gly Met Ser Pro Trp Gln
    50                  55                  60

Val Met Leu Phe Arg Lys Ser Pro Gln Glu Leu Leu Cys Gly Ala Ser
65                  70                  75                  80
```

```
Leu Ile Ser Asp Arg Trp Val Leu Thr Ala Ala His Cys Leu Leu Tyr
             85                  90                  95

Pro Pro Trp Asp Lys Asn Phe Thr Glu Asn Asp Leu Leu Val Arg Ile
        100                 105                 110

Gly Lys His Ser Arg Thr Arg Tyr Glu Arg Asn Ile Glu Lys Ile Ser
            115                 120                 125

Met Leu Glu Lys Ile Tyr Ile His Pro Arg Tyr Asn Trp Arg Glu Asn
    130                 135                 140

Leu Asp Arg Asp Ile Ala Leu Met Lys Leu Lys Pro Val Ala Phe
145                 150                 155                 160

Ser Asp Tyr Ile His Pro Val Cys Leu Pro Asp Arg Glu Thr Ala Ala
                165                 170                 175

Ser Leu Leu Gln Ala Gly Tyr Lys Gly Arg Val Thr Gly Trp Gly Asn
        180                 185                 190

Leu Lys Glu Thr Trp Thr Ala Asn Val Gly Lys Gly Gln Pro Ser Val
            195                 200                 205

Leu Gln Val Val Asn Leu Pro Ile Val Glu Arg Pro Val Cys Lys Asp
    210                 215                 220

Ser Thr Arg Ile Arg Ile Thr Asp Asn Met Phe Cys Ala Gly Tyr Lys
225                 230                 235                 240

Pro Asp Glu Gly Lys Arg Gly Asp Ala Cys Glu Gly Asp Ser Gly Gly
                245                 250                 255

Pro Phe Val Met Lys Ser Pro Phe Asn Asn Arg Trp Tyr Gln Met Gly
            260                 265                 270

Ile Val Ser Trp Gly Glu Gly Cys Asp Arg Asp Gly Lys Tyr Gly Phe
        275                 280                 285

Tyr Thr His Val Phe Arg Leu Lys Lys Trp Ile Gln Lys Val Ile Asp
    290                 295                 300

Gln Phe Gly Glu
305

<210> SEQ ID NO 3
<211> LENGTH: 1056
<212> TYPE: DNA
<213> ORGANISM: Homo sapiens
<220> FEATURE:
<221> NAME/KEY: CDS
<222> LOCATION: (1)..(1056)

<400> SEQUENCE: 3 atg gcg cac gtc cga ggc ttg cag ctg cct ggc tgc ctg gcc ctg gct      48
Met Ala His Val Arg Gly Leu Gln Leu Pro Gly Cys Leu Ala Leu Ala
1               5                   10                  15 gcc ctg tgt agc ctt gtg cac agc cag cat gtg ttc ctg gct cct cag      96
Ala Leu Cys Ser Leu Val His Ser Gln His Val Phe Leu Ala Pro Gln
            20                  25                  30 caa gca cgg tcg ctg ctc cag cgg gtc cgg cga acc gcc acc agt gag     144
Gln Ala Arg Ser Leu Leu Gln Arg Val Arg Arg Thr Ala Thr Ser Glu
        35                  40                  45 tac cag act ttc ttc aat ccg agg acc ttt ggc tcg gga gag gca gac     192
Tyr Gln Thr Phe Phe Asn Pro Arg Thr Phe Gly Ser Gly Glu Ala Asp
50                  55                  60 tgt ggg ctg cga cct ctg ttc gag aag aag tcg ctg gag gac aaa acc     240
Cys Gly Leu Arg Pro Leu Phe Glu Lys Lys Ser Leu Glu Asp Lys Thr
65                  70                  75                  80 gaa aga gag ctc ctg gaa tcc tac atc gac ggg cgc att gtg gag ggc     288
Glu Arg Glu Leu Leu Glu Ser Tyr Ile Asp Gly Arg Ile Val Glu Gly
                85                  90                  95
```

| | | |
|---|---|---|
| tcg gat gca gag atc ggc atg tca cct tgg cag gtg atg ctt ttc cgg<br>Ser Asp Ala Glu Ile Gly Met Ser Pro Trp Gln Val Met Leu Phe Arg<br>          100                     105                 110 | | 336 |
| aag agt ccc cag gag ctg ctg tgt ggg gcc agc ctc atc agt gac cgc<br>Lys Ser Pro Gln Glu Leu Leu Cys Gly Ala Ser Leu Ile Ser Asp Arg<br>          115                     120                 125 | | 384 |
| tgg gtc ctc acc gcc gcc cac tgc ctc ctg tac ccg ccc tgg gac aag<br>Trp Val Leu Thr Ala Ala His Cys Leu Leu Tyr Pro Pro Trp Asp Lys<br>130                     135                 140 | | 432 |
| aac ttc acc gag aat gac ctt ctg gtg cgc att ggc aag cac tcc cgc<br>Asn Phe Thr Glu Asn Asp Leu Leu Val Arg Ile Gly Lys His Ser Arg<br>145                     150                 155                 160 | | 480 |
| aca agg tac gag cga aac att gaa aag ata tcc atg ttg gaa aag atc<br>Thr Arg Tyr Glu Arg Asn Ile Glu Lys Ile Ser Met Leu Glu Lys Ile<br>                 165                 170                 175 | | 528 |
| tac atc cac ccc agg tac aac tgg cgg gag aac ctg gac cgg gac att<br>Tyr Ile His Pro Arg Tyr Asn Trp Arg Glu Asn Leu Asp Arg Asp Ile<br>          180                     185                 190 | | 576 |
| gcc ctg atg aag ctg aag aag cct gtt gcc ttc agt gac tac att cac<br>Ala Leu Met Lys Leu Lys Lys Pro Val Ala Phe Ser Asp Tyr Ile His<br>                 195                 200                 205 | | 624 |
| cct gtg tgt ctg ccc gac agg gag acg gca gcc agc ttg ctc cag gct<br>Pro Val Cys Leu Pro Asp Arg Glu Thr Ala Ala Ser Leu Leu Gln Ala<br>210                     215                 220 | | 672 |
| gga tac aag ggg cgg gtg aca ggc tgg ggc aac ctg aag gag acg tgg<br>Gly Tyr Lys Gly Arg Val Thr Gly Trp Gly Asn Leu Lys Glu Thr Trp<br>225                     230                 235                 240 | | 720 |
| aca gcc aac gtt ggt aag ggg cag ccc agt gtc ctg cag gtg gtg aac<br>Thr Ala Asn Val Gly Lys Gly Gln Pro Ser Val Leu Gln Val Val Asn<br>                 245                 250                 255 | | 768 |
| ctg ccc att gtg gag cgg ccg gtc tgc aag gac tcc acc cgg atc cgc<br>Leu Pro Ile Val Glu Arg Pro Val Cys Lys Asp Ser Thr Arg Ile Arg<br>          260                     265                 270 | | 816 |
| atc act gac aac atg ttc tgt gct ggt tac aag cct gat gaa ggg aaa<br>Ile Thr Asp Asn Met Phe Cys Ala Gly Tyr Lys Pro Asp Glu Gly Lys<br>275                     280                 285 | | 864 |
| cga ggg gat gcc tgt gaa ggt gac agt ggg gga ccc ttt gtc atg aag<br>Arg Gly Asp Ala Cys Glu Gly Asp Ser Gly Gly Pro Phe Val Met Lys<br>290                     295                 300 | | 912 |
| agc ccc ttt aac aac cgc tgg tat caa atg ggc atc gtc tca tgg ggt<br>Ser Pro Phe Asn Asn Arg Trp Tyr Gln Met Gly Ile Val Ser Trp Gly<br>305                     310                 315                 320 | | 960 |
| gaa ggc tgt gac cgg gat ggg aaa tat ggc ttc tac aca cat gtg ttc<br>Glu Gly Cys Asp Arg Asp Gly Lys Tyr Gly Phe Tyr Thr His Val Phe<br>                 325                 330                 335 | | 1008 |
| cgc ctg aag aag tgg ata cag aag gtc att gat cag ttt gga gag tag<br>Arg Leu Lys Lys Trp Ile Gln Lys Val Ile Asp Gln Phe Gly Glu<br>          340                     345                 350 | | 1056 |

<210> SEQ ID NO 4
<211> LENGTH: 351
<212> TYPE: PRT
<213> ORGANISM: Homo sapiens

<400> SEQUENCE: 4

Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Thr Ala Thr Ser Glu
        35                  40                  45

-continued

```
Tyr Gln Thr Phe Phe Asn Pro Arg Thr Phe Gly Ser Gly Glu Ala Asp
 50                  55                  60

Cys Gly Leu Arg Pro Leu Phe Glu Lys Lys Ser Leu Glu Asp Lys Thr
 65                  70                  75                  80

Glu Arg Glu Leu Leu Glu Ser Tyr Ile Asp Gly Arg Ile Val Glu Gly
                 85                  90                  95

Ser Asp Ala Glu Ile Gly Met Ser Pro Trp Gln Val Met Leu Phe Arg
             100                 105                 110

Lys Ser Pro Gln Glu Leu Leu Cys Gly Ala Ser Leu Ile Ser Asp Arg
         115                 120                 125

Trp Val Leu Thr Ala Ala His Cys Leu Leu Tyr Pro Pro Trp Asp Lys
130                 135                 140

Asn Phe Thr Glu Asn Asp Leu Leu Val Arg Ile Gly Lys His Ser Arg
145                 150                 155                 160

Thr Arg Tyr Glu Arg Asn Ile Glu Lys Ile Ser Met Leu Glu Lys Ile
                165                 170                 175

Tyr Ile His Pro Arg Tyr Asn Trp Arg Glu Asn Leu Asp Arg Asp Ile
            180                 185                 190

Ala Leu Met Lys Leu Lys Lys Pro Val Ala Phe Ser Asp Tyr Ile His
        195                 200                 205

Pro Val Cys Leu Pro Asp Arg Glu Thr Ala Ala Ser Leu Leu Gln Ala
210                 215                 220

Gly Tyr Lys Gly Arg Val Thr Gly Trp Gly Asn Leu Lys Glu Thr Trp
225                 230                 235                 240

Thr Ala Asn Val Gly Lys Gly Gln Pro Ser Val Leu Gln Val Val Asn
                245                 250                 255

Leu Pro Ile Val Glu Arg Pro Val Cys Lys Asp Ser Thr Arg Ile Arg
            260                 265                 270

Ile Thr Asp Asn Met Phe Cys Ala Gly Tyr Lys Pro Asp Glu Gly Lys
        275                 280                 285

Arg Gly Asp Ala Cys Glu Gly Asp Ser Gly Gly Pro Phe Val Met Lys
290                 295                 300

Ser Pro Phe Asn Asn Arg Trp Tyr Gln Met Gly Ile Val Ser Trp Gly
305                 310                 315                 320

Glu Gly Cys Asp Arg Asp Gly Lys Tyr Gly Phe Tyr Thr His Val Phe
                325                 330                 335

Arg Leu Lys Lys Trp Ile Gln Lys Val Ile Asp Gln Phe Gly Glu
            340                 345                 350

<210> SEQ ID NO 5
<211> LENGTH: 1056
<212> TYPE: DNA
<213> ORGANISM: Homo sapiens
<220> FEATURE:
<221> NAME/KEY: CDS
<222> LOCATION: (1)..(1056)

<400> SEQUENCE: 5 atg gcg cac gtc cga ggc ttg cag ctg cct ggc tgc ctg gcc ctg gct      48
Met Ala His Val Arg Gly Leu Gln Leu Pro Gly Cys Leu Ala Leu Ala
  1               5                  10                  15 gcc ctg tgt agc ctt gtg cac agc cag cat gtg ttc ctg gct cct cag      96
Ala Leu Cys Ser Leu Val His Ser Gln His Val Phe Leu Ala Pro Gln
             20                  25                  30 caa gca cgg tcg ctg ctc cag cgg gtc cgg cga acc gcc acc agt gag     144
Gln Ala Arg Ser Leu Leu Gln Arg Val Arg Arg Thr Ala Thr Ser Glu
         35                  40                  45
```

| | |
|---|---:|
| tac cag act ttc ttc aat ccg agg acc ttt ggc tcg gga gag gca gac<br>Tyr Gln Thr Phe Phe Asn Pro Arg Thr Phe Gly Ser Gly Glu Ala Asp<br>    50                          55                        60 | 192 |
| tgt ggg ctg cga cct ctg ttc gag aag aag tcg ctg gag gac aaa acc<br>Cys Gly Leu Arg Pro Leu Phe Glu Lys Lys Ser Leu Glu Asp Lys Thr<br>65                       70                        75                        80 | 240 |
| gaa aga gag ctc ctg gaa tcc tac atc gac ggg cgc att gtg gag ggc<br>Glu Arg Glu Leu Leu Glu Ser Tyr Ile Asp Gly Arg Ile Val Glu Gly<br>                      85                        90                        95 | 288 |
| tcg gat gca gag atc ggc atg tca cct tgg cag gtg atg ctt ttc cgg<br>Ser Asp Ala Glu Ile Gly Met Ser Pro Trp Gln Val Met Leu Phe Arg<br>                100                        105                     110 | 336 |
| aag agt ccc cag gag ctg ctg tgt ggg gcc agc ctc atc agt gac cgc<br>Lys Ser Pro Gln Glu Leu Leu Cys Gly Ala Ser Leu Ile Ser Asp Arg<br>               115                      120                       125 | 384 |
| tgg gtc ctc acc gcc gcc gcc tgc ctc ctg tac ccg ccc tgg gac aag<br>Trp Val Leu Thr Ala Ala Ala Cys Leu Leu Tyr Pro Pro Trp Asp Lys<br>130                     135                      140 | 432 |
| aac ttc acc gag aat gac ctt ctg gtg cgc att ggc gcc cac tcc cgc<br>Asn Phe Thr Glu Asn Asp Leu Leu Val Arg Ile Gly Ala His Ser Arg<br>145                     150                      155                     160 | 480 |
| aca agg tac gag cga aac att gaa aag ata tcc atg ttg gaa aag atc<br>Thr Arg Tyr Glu Arg Asn Ile Glu Lys Ile Ser Met Leu Glu Lys Ile<br>                     165                       170                     175 | 528 |
| tac atc cac ccc gcc tac aac tgg cgg gag aac ctg gac cgg gac att<br>Tyr Ile His Pro Ala Tyr Asn Trp Arg Glu Asn Leu Asp Arg Asp Ile<br>                    180                      185                   190 | 576 |
| gcc ctg atg aag ctg aag aag cct gtt gcc ttc agt gac tac att cac<br>Ala Leu Met Lys Leu Lys Lys Pro Val Ala Phe Ser Asp Tyr Ile His<br>               195                      200                     205 | 624 |
| cct gtg tgt ctg ccc gac agg gag acg gca gcc agc ttg ctc cag gct<br>Pro Val Cys Leu Pro Asp Arg Glu Thr Ala Ala Ser Leu Leu Gln Ala<br>210                     215                      220 | 672 |
| gga tac aag ggg cgg gtg aca ggc tgg ggc aac ctg aag gag acg tgg<br>Gly Tyr Lys Gly Arg Val Thr Gly Trp Gly Asn Leu Lys Glu Thr Trp<br>225                     230                      235                     240 | 720 |
| aca gcc aac gtt ggt aag ggg cag ccc agt gtc ctg cag gtg gtg aac<br>Thr Ala Asn Val Gly Lys Gly Gln Pro Ser Val Leu Gln Val Val Asn<br>                    245                      250                     255 | 768 |
| ctg ccc att gtg gag cgg ccg gtc tgc aag gac tcc acc cgg atc cgc<br>Leu Pro Ile Val Glu Arg Pro Val Cys Lys Asp Ser Thr Arg Ile Arg<br>                    260                      265                     270 | 816 |
| atc act gac aac atg ttc tgt gct ggt tac aag cct gat gaa ggg aaa<br>Ile Thr Asp Asn Met Phe Cys Ala Gly Tyr Lys Pro Asp Glu Gly Lys<br>               275                      280                     285 | 864 |
| cga ggg gat gcc tgt gaa ggg gac gcc ggg gga ccc ttt gtc atg aag<br>Arg Gly Asp Ala Cys Glu Gly Asp Ala Gly Gly Pro Phe Val Met Lys<br>290                     295                      300 | 912 |
| agc ccc ttt aac aac cgc tgg tat caa atg ggc atc gtc tca tgg ggt<br>Ser Pro Phe Asn Asn Arg Trp Tyr Gln Met Gly Ile Val Ser Trp Gly<br>305                     310                      315                     320 | 960 |
| gaa ggc tgt gac cgg gat ggg aaa tat ggc ttc tac aca cat gtg ttc<br>Glu Gly Cys Asp Arg Asp Gly Lys Tyr Gly Phe Tyr Thr His Val Phe<br>                    325                      330                     335 | 1008 |
| cgc ctg aag aag tgg ata cag aag gtc att gat cag ttt gga gag tag<br>Arg Leu Lys Lys Trp Ile Gln Lys Val Ile Asp Gln Phe Gly Glu<br>               340                      345                     350 | 1056 |

<210> SEQ ID NO 6
<211> LENGTH: 351

<212> TYPE: PRT
<213> ORGANISM: Homo sapiens

<400> SEQUENCE: 6

Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Thr Ala Thr Ser Glu
        35                  40                  45

Tyr Gln Thr Phe Phe Asn Pro Arg Thr Phe Gly Ser Gly Glu Ala Asp
    50                  55                  60

Cys Gly Leu Arg Pro Leu Phe Glu Lys Lys Ser Leu Glu Asp Lys Thr
65                  70                  75                  80

Glu Arg Glu Leu Leu Glu Ser Tyr Ile Asp Gly Arg Ile Val Glu Gly
                85                  90                  95

Ser Asp Ala Glu Ile Gly Met Ser Pro Trp Gln Val Met Leu Phe Arg
            100                 105                 110

Lys Ser Pro Gln Glu Leu Leu Cys Gly Ala Ser Leu Ile Ser Asp Arg
        115                 120                 125

Trp Val Leu Thr Ala Ala Cys Leu Leu Tyr Pro Pro Trp Asp Lys
    130                 135                 140

Asn Phe Thr Glu Asn Asp Leu Leu Val Arg Ile Gly Ala His Ser Arg
145                 150                 155                 160

Thr Arg Tyr Glu Arg Asn Ile Glu Lys Ile Ser Met Leu Glu Lys Ile
                165                 170                 175

Tyr Ile His Pro Ala Tyr Asn Trp Arg Glu Asn Leu Asp Arg Asp Ile
            180                 185                 190

Ala Leu Met Lys Leu Lys Lys Pro Val Ala Phe Ser Asp Tyr Ile His
        195                 200                 205

Pro Val Cys Leu Pro Asp Arg Glu Thr Ala Ala Ser Leu Leu Gln Ala
    210                 215                 220

Gly Tyr Lys Gly Arg Val Thr Gly Trp Gly Asn Leu Lys Glu Thr Trp
225                 230                 235                 240

Thr Ala Asn Val Gly Lys Gly Gln Pro Ser Val Leu Gln Val Val Asn
                245                 250                 255

Leu Pro Ile Val Glu Arg Pro Val Cys Lys Asp Ser Thr Arg Ile Arg
            260                 265                 270

Ile Thr Asp Asn Met Phe Cys Ala Gly Tyr Lys Pro Asp Glu Gly Lys
        275                 280                 285

Arg Gly Asp Ala Cys Glu Gly Asp Ala Gly Gly Pro Phe Val Met Lys
    290                 295                 300

Ser Pro Phe Asn Asn Arg Trp Tyr Gln Met Gly Ile Val Ser Trp Gly
305                 310                 315                 320

Glu Gly Cys Asp Arg Asp Gly Lys Tyr Gly Phe Tyr Thr His Val Phe
                325                 330                 335

Arg Leu Lys Lys Trp Ile Gln Lys Val Ile Asp Gln Phe Gly Glu
            340                 345                 350

<210> SEQ ID NO 7
<211> LENGTH: 1056
<212> TYPE: DNA
<213> ORGANISM: Homo sapiens
<220> FEATURE:
<221> NAME/KEY: CDS
<222> LOCATION: (1)..(1056)

<400> SEQUENCE: 7

```
atg gcg cac gtc cga ggc ttg cag ctg cct ggc tgc ctg gcc ctg gct        48
Met Ala His Val Arg Gly Leu Gln Leu Pro Gly Cys Leu Ala Leu Ala
1               5                   10                  15 gcc ctg tgt agc ctt gtg cac agc cag cat gtg ttc ctg gct cct cag        96
Ala Leu Cys Ser Leu Val His Ser Gln His Val Phe Leu Ala Pro Gln
            20                  25                  30 caa gca cgg tcg ctg ctc cag cgg gtc cgg cga acc gcc acc agt gag       144
Gln Ala Arg Ser Leu Leu Gln Arg Val Arg Arg Thr Ala Thr Ser Glu
        35                  40                  45 tac cag act ttc ttc aat ccg agg acc ttt ggc tcg gga gag gca gac       192
Tyr Gln Thr Phe Phe Asn Pro Arg Thr Phe Gly Ser Gly Glu Ala Asp
    50                  55                  60 tgt ggg ctg cga cct ctg ttc gag aag aag tcg ctg gag gac aaa acc       240
Cys Gly Leu Arg Pro Leu Phe Glu Lys Lys Ser Leu Glu Asp Lys Thr
65                  70                  75                  80 gaa aga gag ctc ctg gaa tcc tac atc gac ggg cgc att gtg gag ggc       288
Glu Arg Glu Leu Leu Glu Ser Tyr Ile Asp Gly Arg Ile Val Glu Gly
                85                  90                  95 tcg gat gca gag atc ggc atg tca cct tgg cag gtg atg ctt ttc cgg       336
Ser Asp Ala Glu Ile Gly Met Ser Pro Trp Gln Val Met Leu Phe Arg
            100                 105                 110 aag agt ccc cag gag ctg ctg tgt ggg gcc agc ctc atc agt gac cgc       384
Lys Ser Pro Gln Glu Leu Leu Cys Gly Ala Ser Leu Ile Ser Asp Arg
        115                 120                 125 tgg gtc ctc acc gcc gcc gcc tgc ctc ctg tac ccg ccc tgg gac aag       432
Trp Val Leu Thr Ala Ala Ala Cys Leu Leu Tyr Pro Pro Trp Asp Lys
    130                 135                 140 aac ttc acc gag aat gac ctt ctg gtg cgc att ggc aag cac tcc cgc       480
Asn Phe Thr Glu Asn Asp Leu Leu Val Arg Ile Gly Lys His Ser Arg
145                 150                 155                 160 aca agg tac gag cga aac att gaa aag ata tcc atg ttg gaa aag atc       528
Thr Arg Tyr Glu Arg Asn Ile Glu Lys Ile Ser Met Leu Glu Lys Ile
                165                 170                 175 tac atc cac ccc agg tac aac tgg cgg gag aac ctg gac cgg gac att       576
Tyr Ile His Pro Arg Tyr Asn Trp Arg Glu Asn Leu Asp Arg Asp Ile
            180                 185                 190 gcc ctg atg aag ctg aag aag cct gtt gcc ttc agt gac tac att cac       624
Ala Leu Met Lys Leu Lys Lys Pro Val Ala Phe Ser Asp Tyr Ile His
        195                 200                 205 cct gtg tgt ctg ccc gac agg gag acg gca gcc agc ttg ctc cag gct       672
Pro Val Cys Leu Pro Asp Arg Glu Thr Ala Ala Ser Leu Leu Gln Ala
    210                 215                 220 gga tac aag ggg cgg gtg aca ggc tgg ggc aac ctg aag gag acg tgg       720
Gly Tyr Lys Gly Arg Val Thr Gly Trp Gly Asn Leu Lys Glu Thr Trp
225                 230                 235                 240 aca gcc aac gtt ggt aag ggg cag ccc agt gtc ctg cag gtg gtg aac       768
Thr Ala Asn Val Gly Lys Gly Gln Pro Ser Val Leu Gln Val Val Asn
                245                 250                 255 ctg ccc att gtg gag cgg ccg gtc tgc aag gac tcc acc cgg atc cgc       816
Leu Pro Ile Val Glu Arg Pro Val Cys Lys Asp Ser Thr Arg Ile Arg
            260                 265                 270 atc act gac aac atg ttc tgt gct ggt tac aag cct gat gaa ggg aaa       864
Ile Thr Asp Asn Met Phe Cys Ala Gly Tyr Lys Pro Asp Glu Gly Lys
        275                 280                 285 cga ggg gat gcc tgt gaa ggg gac gcc ggg gga ccc ttt gtc atg aag       912
Arg Gly Asp Ala Cys Glu Gly Asp Ala Gly Gly Pro Phe Val Met Lys
    290                 295                 300 agc ccc ttt aac aac cgc tgg tat caa atg ggc atc gtc tca tgg ggt       960
Ser Pro Phe Asn Asn Arg Trp Tyr Gln Met Gly Ile Val Ser Trp Gly
```

```
                305                 310                 315                 320
gaa ggc tgt gac cgg gat ggg aaa tat ggc ttc tac aca cat gtg ttc      1008
Glu Gly Cys Asp Arg Asp Gly Lys Tyr Gly Phe Tyr Thr His Val Phe
                325                 330                 335 cgc ctg aag aag tgg ata cag aag gtc att gat cag ttt gga gag tag      1056
Arg Leu Lys Lys Trp Ile Gln Lys Val Ile Asp Gln Phe Gly Glu
                340                 345                 350

<210> SEQ ID NO 8
<211> LENGTH: 351
<212> TYPE: PRT
<213> ORGANISM: Homo sapiens

<400> SEQUENCE: 8

Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
                20                  25                  30

Gln Ala Arg Ser Leu Leu Gln Arg Val Arg Arg Thr Ala Thr Ser Glu
            35                  40                  45

Tyr Gln Thr Phe Phe Asn Pro Arg Thr Phe Gly Ser Gly Glu Ala Asp
        50                  55                  60

Cys Gly Leu Arg Pro Leu Phe Glu Lys Lys Ser Leu Glu Asp Lys Thr
65                  70                  75                  80

Glu Arg Glu Leu Leu Glu Ser Tyr Ile Asp Gly Arg Ile Val Glu Gly
                85                  90                  95

Ser Asp Ala Glu Ile Gly Met Ser Pro Trp Gln Val Met Leu Phe Arg
            100                 105                 110

Lys Ser Pro Gln Glu Leu Leu Cys Gly Ala Ser Leu Ile Ser Asp Arg
        115                 120                 125

Trp Val Leu Thr Ala Ala Cys Leu Leu Tyr Pro Pro Trp Asp Lys
    130                 135                 140

Asn Phe Thr Glu Asn Asp Leu Leu Val Arg Ile Gly Lys His Ser Arg
145                 150                 155                 160

Thr Arg Tyr Glu Arg Asn Ile Glu Lys Ile Ser Met Leu Glu Lys Ile
                165                 170                 175

Tyr Ile His Pro Arg Tyr Asn Trp Arg Glu Asn Leu Asp Arg Asp Ile
            180                 185                 190

Ala Leu Met Lys Leu Lys Lys Pro Val Ala Phe Ser Asp Tyr Ile His
        195                 200                 205

Pro Val Cys Leu Pro Asp Arg Glu Thr Ala Ala Ser Leu Leu Gln Ala
    210                 215                 220

Gly Tyr Lys Gly Arg Val Thr Gly Trp Gly Asn Leu Lys Glu Thr Trp
225                 230                 235                 240

Thr Ala Asn Val Gly Lys Gly Gln Pro Ser Val Leu Gln Val Val Asn
                245                 250                 255

Leu Pro Ile Val Glu Arg Pro Val Cys Lys Asp Ser Thr Arg Ile Arg
            260                 265                 270

Ile Thr Asp Asn Met Phe Cys Ala Gly Tyr Lys Pro Asp Glu Gly Lys
        275                 280                 285

Arg Gly Asp Ala Cys Glu Gly Asp Ala Gly Gly Pro Phe Val Met Lys
    290                 295                 300

Ser Pro Phe Asn Asn Arg Trp Tyr Gln Met Gly Ile Val Ser Trp Gly
305                 310                 315                 320

Glu Gly Cys Asp Arg Asp Gly Lys Tyr Gly Phe Tyr Thr His Val Phe
                325                 330                 335
```

```
Arg Leu Lys Lys Trp Ile Gln Lys Val Ile Asp Gln Phe Gly Glu
        340                 345                 350
```

<210> SEQ ID NO 9
<211> LENGTH: 1056
<212> TYPE: DNA
<213> ORGANISM: Homo sapiens
<220> FEATURE:
<221> NAME/KEY: CDS
<222> LOCATION: (1)..(1056)

<400> SEQUENCE: 9

```
atg gcg cac gtc cga ggc ttg cag ctg cct ggc tgc ctg gcc ctg gct      48
Met Ala His Val Arg Gly Leu Gln Leu Pro Gly Cys Leu Ala Leu Ala
1               5                   10                  15 gcc ctg tgt agc ctt gtg cac agc cag cat gtg ttc ctg gct cct cag     96
Ala Leu Cys Ser Leu Val His Ser Gln His Val Phe Leu Ala Pro Gln
            20                  25                  30 caa gca cgg tcg ctg ctc cag cgg gtc cgg cga acc gcc acc agt gag    144
Gln Ala Arg Ser Leu Leu Gln Arg Val Arg Arg Thr Ala Thr Ser Glu
        35                  40                  45 tac cag act ttc ttc aat ccg agg acc ttt ggc tcg gga gag gca gac    192
Tyr Gln Thr Phe Phe Asn Pro Arg Thr Phe Gly Ser Gly Glu Ala Asp
    50                  55                  60 tgt ggg ctg cga cct ctg ttc gag aag aag tcg ctg gag gac aaa acc    240
Cys Gly Leu Arg Pro Leu Phe Glu Lys Lys Ser Leu Glu Asp Lys Thr
65                  70                  75                  80 gaa aga gag ctc ctg gaa tcc tac atc gac ggg cgc att gtg gag ggc    288
Glu Arg Glu Leu Leu Glu Ser Tyr Ile Asp Gly Arg Ile Val Glu Gly
                85                  90                  95 tcg gat gca gag atc ggc atg tca cct tgg cag gtg atg ctt ttc cgg    336
Ser Asp Ala Glu Ile Gly Met Ser Pro Trp Gln Val Met Leu Phe Arg
            100                 105                 110 aag agt ccc cag gag ctg ctg tgt ggg gcc agc ctc atc agt gac cgc    384
Lys Ser Pro Gln Glu Leu Leu Cys Gly Ala Ser Leu Ile Ser Asp Arg
        115                 120                 125 tgg gtc ctc acc gcc gcc gcc tgc ctc ctg tac ccg ccc tgg gac aag    432
Trp Val Leu Thr Ala Ala Ala Cys Leu Leu Tyr Pro Pro Trp Asp Lys
    130                 135                 140 aac ttc acc gag aat gac ctt ctg gtg cgc att ggc gcc cac tcc cgc    480
Asn Phe Thr Glu Asn Asp Leu Leu Val Arg Ile Gly Ala His Ser Arg
145                 150                 155                 160 aca agg tac gag cga aac att gaa aag ata tcc atg ttg gaa aag atc    528
Thr Arg Tyr Glu Arg Asn Ile Glu Lys Ile Ser Met Leu Glu Lys Ile
                165                 170                 175 tac atc cac ccc agg tac aac tgg cgg gag aac ctg gac cgg gac att    576
Tyr Ile His Pro Arg Tyr Asn Trp Arg Glu Asn Leu Asp Arg Asp Ile
            180                 185                 190 gcc ctg atg aag ctg aag aag cct gtt gcc ttc agt gac tac att cac    624
Ala Leu Met Lys Leu Lys Lys Pro Val Ala Phe Ser Asp Tyr Ile His
        195                 200                 205 cct gtg tgt ctg ccc gac agg gag acg gca gcc agc ttg ctc cag gct    672
Pro Val Cys Leu Pro Asp Arg Glu Thr Ala Ala Ser Leu Leu Gln Ala
    210                 215                 220 gga tac aag ggg cgg gtg aca ggc tgg ggc aac ctg aag gag acg tgg    720
Gly Tyr Lys Gly Arg Val Thr Gly Trp Gly Asn Leu Lys Glu Thr Trp
225                 230                 235                 240 aca gcc aac gtt ggt aag ggg cag ccc agt gtc ctg cag gtg tga aac    768
Thr Ala Asn Val Gly Lys Gly Gln Pro Ser Val Leu Gln Val Asn
                245                 250                 255 ctg ccc att gtg gag cgg ccg gtc tgc aag gac tcc acc cgg atc cgc    816
Leu Pro Ile Val Glu Arg Pro Val Cys Lys Asp Ser Thr Arg Ile Arg
```

```
Leu Pro Ile Val Glu Arg Pro Val Cys Lys Asp Ser Thr Arg Ile Arg
            260                 265                 270 atc act gac aac atg ttc tgt gct ggt tac aag cct gat gaa ggg aaa      864
Ile Thr Asp Asn Met Phe Cys Ala Gly Tyr Lys Pro Asp Glu Gly Lys
            275                 280                 285 cga ggg gat gcc tgt gaa ggg gac gcc ggg gga ccc ttt gtc atg aag      912
Arg Gly Asp Ala Cys Glu Gly Asp Ala Gly Gly Pro Phe Val Met Lys
        290                 295                 300 agc ccc ttt aac aac cgc tgg tat caa atg ggc atc gtc tca tgg ggt      960
Ser Pro Phe Asn Asn Arg Trp Tyr Gln Met Gly Ile Val Ser Trp Gly
305                 310                 315                 320 gaa ggc tgt gac cgg gat ggg aaa tat ggc ttc tac aca cat gtg ttc     1008
Glu Gly Cys Asp Arg Asp Gly Lys Tyr Gly Phe Tyr Thr His Val Phe
                325                 330                 335 cgc ctg aag aag tgg ata cag aag gtc att gat cag ttt gga gag tag     1056
Arg Leu Lys Lys Trp Ile Gln Lys Val Ile Asp Gln Phe Gly Glu
            340                 345                 350
```

<210> SEQ ID NO 10
<211> LENGTH: 351
<212> TYPE: PRT
<213> ORGANISM: Homo sapiens

<400> SEQUENCE: 10

```
Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Thr Ala Thr Ser Glu
        35                  40                  45

Tyr Gln Thr Phe Phe Asn Pro Arg Thr Phe Gly Ser Gly Glu Ala Asp
    50                  55                  60

Cys Gly Leu Arg Pro Leu Phe Glu Lys Lys Ser Leu Glu Asp Lys Thr
65                  70                  75                  80

Glu Arg Glu Leu Leu Glu Ser Tyr Ile Asp Gly Arg Ile Val Glu Gly
                85                  90                  95

Ser Asp Ala Glu Ile Gly Met Ser Pro Trp Gln Val Met Leu Phe Arg
            100                 105                 110

Lys Ser Pro Gln Glu Leu Leu Cys Gly Ala Ser Leu Ile Ser Asp Arg
        115                 120                 125

Trp Val Leu Thr Ala Ala Cys Leu Leu Tyr Pro Pro Trp Asp Lys
    130                 135                 140

Asn Phe Thr Glu Asn Asp Leu Leu Val Arg Ile Gly Ala His Ser Arg
145                 150                 155                 160

Thr Arg Tyr Glu Arg Asn Ile Glu Lys Ile Ser Met Leu Glu Lys Ile
                165                 170                 175

Tyr Ile His Pro Arg Tyr Asn Trp Arg Glu Asn Leu Asp Arg Asp Ile
            180                 185                 190

Ala Leu Met Lys Leu Lys Lys Pro Val Ala Phe Ser Asp Tyr Ile His
        195                 200                 205

Pro Val Cys Leu Pro Asp Arg Glu Thr Ala Ala Ser Leu Leu Gln Ala
    210                 215                 220

Gly Tyr Lys Gly Arg Val Thr Gly Trp Gly Asn Leu Lys Glu Thr Trp
225                 230                 235                 240

Thr Ala Asn Val Gly Lys Gly Gln Pro Ser Val Leu Gln Val Val Asn
                245                 250                 255

Leu Pro Ile Val Glu Arg Pro Val Cys Lys Asp Ser Thr Arg Ile Arg
```

```
                     260                 265                 270
Ile Thr Asp Asn Met Phe Cys Ala Gly Tyr Lys Pro Asp Glu Gly Lys
            275                 280                 285

Arg Gly Asp Ala Cys Glu Gly Asp Ala Gly Gly Pro Phe Val Met Lys
            290                 295                 300

Ser Pro Phe Asn Asn Arg Trp Tyr Gln Met Gly Ile Val Ser Trp Gly
305                 310                 315                 320

Glu Gly Cys Asp Arg Asp Gly Lys Tyr Gly Phe Tyr Thr His Val Phe
            325                 330                 335

Arg Leu Lys Lys Trp Ile Gln Lys Val Ile Asp Gln Phe Gly Glu
            340                 345                 350

<210> SEQ ID NO 11
<211> LENGTH: 1056
<212> TYPE: DNA
<213> ORGANISM: Homo sapiens
<220> FEATURE:
<221> NAME/KEY: CDS
<222> LOCATION: (1)..(1056)

<400> SEQUENCE: 11 atg gcg cac gtc cga ggc ttg cag ctg cct ggc tgc ctg gcc ctg gct      48
Met Ala His Val Arg Gly Leu Gln Leu Pro Gly Cys Leu Ala Leu Ala
1               5                   10                  15 gcc ctg tgt agc ctt gtg cac agc cag cat gtg ttc ctg gct cct cag      96
Ala Leu Cys Ser Leu Val His Ser Gln His Val Phe Leu Ala Pro Gln
            20                  25                  30 caa gca cgg tcg ctg ctc cag cgg gtc cgg cga acc gcc acc agt gag     144
Gln Ala Arg Ser Leu Leu Gln Arg Val Arg Arg Thr Ala Thr Ser Glu
        35                  40                  45 tac cag act ttc ttc aat ccg agg acc ttt ggc tcg gga gag gca gac     192
Tyr Gln Thr Phe Phe Asn Pro Arg Thr Phe Gly Ser Gly Glu Ala Asp
    50                  55                  60 tgt ggg ctg cga cct ctg ttc gag aag aag tcg ctg gag gac aaa acc     240
Cys Gly Leu Arg Pro Leu Phe Glu Lys Lys Ser Leu Glu Asp Lys Thr
65                  70                  75                  80 gaa aga gag ctc ctg gaa tcc tac atc gac ggg cgc att gtg gag ggc     288
Glu Arg Glu Leu Leu Glu Ser Tyr Ile Asp Gly Arg Ile Val Glu Gly
                85                  90                  95 tcg gat gca gag atc ggc atg tca cct tgg cag gtg atg ctt ttc cgg     336
Ser Asp Ala Glu Ile Gly Met Ser Pro Trp Gln Val Met Leu Phe Arg
            100                 105                 110 aag agt ccc cag gag ctg ctg tgt ggg gcc agc ctc atc agt gac cgc     384
Lys Ser Pro Gln Glu Leu Leu Cys Gly Ala Ser Leu Ile Ser Asp Arg
        115                 120                 125 tgg gtc ctc acc gcc gcc gcc tgc ctc ctg tac ccg ccc tgg gac aag     432
Trp Val Leu Thr Ala Ala Ala Cys Leu Leu Tyr Pro Pro Trp Asp Lys
    130                 135                 140 aac ttc acc gag aat gac ctt ctg gtg cgc att ggc gcc cac tcc cgc     480
Asn Phe Thr Glu Asn Asp Leu Leu Val Arg Ile Gly Ala His Ser Arg
145                 150                 155                 160 cag agg tac gag cga aac att gaa aag ata tcc atg ttg gaa aag atc     528
Gln Arg Tyr Glu Arg Asn Ile Glu Lys Ile Ser Met Leu Glu Lys Ile
                165                 170                 175 tac atc cac ccc agg tac aac tgg cgg gag aac ctg gac cgg gac att     576
Tyr Ile His Pro Arg Tyr Asn Trp Arg Glu Asn Leu Asp Arg Asp Ile
            180                 185                 190 gcc ctg atg aag ctg aag aag cct gtt gcc ttc agt gac tac att cac     624
Ala Leu Met Lys Leu Lys Lys Pro Val Ala Phe Ser Asp Tyr Ile His
        195                 200                 205
```

```
cct gtg tgt ctg ccc gac agg gag acg gca gcc agc ttg ctc cag gct        672
Pro Val Cys Leu Pro Asp Arg Glu Thr Ala Ala Ser Leu Leu Gln Ala
    210                 215                 220 gga tac aag ggg cgg gtg aca ggc tgg ggc aac ctg aag gag acg tgg        720
Gly Tyr Lys Gly Arg Val Thr Gly Trp Gly Asn Leu Lys Glu Thr Trp
225                 230                 235                 240 aca gcc aac gtt ggt aag ggg cag ccc agt gtc ctg cag gtg gtg aac        768
Thr Ala Asn Val Gly Lys Gly Gln Pro Ser Val Leu Gln Val Val Asn
                245                 250                 255 ctg ccc att gtg gag cgg ccg gtc tgc aag gac tcc acc cgg atc cgc        816
Leu Pro Ile Val Glu Arg Pro Val Cys Lys Asp Ser Thr Arg Ile Arg
            260                 265                 270 atc act gac aac atg ttc tgt gct ggt tac aag cct gat gaa ggg aaa        864
Ile Thr Asp Asn Met Phe Cys Ala Gly Tyr Lys Pro Asp Glu Gly Lys
        275                 280                 285 cga ggg gat gcc tgt gaa ggg gac gcc ggg gga ccc ttt gtc atg aag        912
Arg Gly Asp Ala Cys Glu Gly Asp Ala Gly Gly Pro Phe Val Met Lys
    290                 295                 300 agc ccc ttt aac aac cgc tgg tat caa atg ggc atc gtc tca tgg ggt        960
Ser Pro Phe Asn Asn Arg Trp Tyr Gln Met Gly Ile Val Ser Trp Gly
305                 310                 315                 320 gaa ggc tgt gac cgg gat ggg aaa tat ggc ttc tac aca cat gtg ttc       1008
Glu Gly Cys Asp Arg Asp Gly Lys Tyr Gly Phe Tyr Thr His Val Phe
                325                 330                 335 cgc ctg aag aag tgg ata cag aag gtc att gat cag ttt gga gag tag       1056
Arg Leu Lys Lys Trp Ile Gln Lys Val Ile Asp Gln Phe Gly Glu
            340                 345                 350
```

<210> SEQ ID NO 12
<211> LENGTH: 351
<212> TYPE: PRT
<213> ORGANISM: Homo sapiens

<400> SEQUENCE: 12

```
Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Thr Ala Thr Ser Glu
        35                  40                  45

Tyr Gln Thr Phe Phe Asn Pro Arg Thr Phe Gly Ser Gly Glu Ala Asp
    50                  55                  60

Cys Gly Leu Arg Pro Leu Phe Glu Lys Lys Ser Leu Glu Asp Lys Thr
65                  70                  75                  80

Glu Arg Glu Leu Leu Glu Ser Tyr Ile Asp Gly Arg Ile Val Glu Gly
                85                  90                  95

Ser Asp Ala Glu Ile Gly Met Ser Pro Trp Gln Val Met Leu Phe Arg
            100                 105                 110

Lys Ser Pro Gln Glu Leu Leu Cys Gly Ala Ser Leu Ile Ser Asp Arg
        115                 120                 125

Trp Val Leu Thr Ala Ala Cys Leu Leu Tyr Pro Pro Trp Asp Lys
    130                 135                 140

Asn Phe Thr Glu Asn Asp Leu Leu Val Arg Ile Gly Ala His Ser Arg
145                 150                 155                 160

Gln Arg Tyr Glu Arg Asn Ile Glu Lys Ile Ser Met Leu Glu Lys Ile
                165                 170                 175

Tyr Ile His Pro Arg Tyr Asn Trp Arg Glu Asn Leu Asp Arg Asp Ile
            180                 185                 190
```

```
Ala Leu Met Lys Leu Lys Lys Pro Val Ala Phe Ser Asp Tyr Ile His
    195                 200                 205

Pro Val Cys Leu Pro Asp Arg Glu Thr Ala Ala Ser Leu Leu Gln Ala
210                 215                 220

Gly Tyr Lys Gly Arg Val Thr Gly Trp Gly Asn Leu Lys Glu Thr Trp
225                 230                 235                 240

Thr Ala Asn Val Gly Lys Gly Gln Pro Ser Val Leu Gln Val Asn
                245                 250                 255

Leu Pro Ile Val Glu Arg Pro Val Cys Lys Asp Ser Thr Arg Ile Arg
                260                 265                 270

Ile Thr Asp Asn Met Phe Cys Ala Gly Tyr Lys Pro Asp Glu Gly Lys
            275                 280                 285

Arg Gly Asp Ala Cys Glu Gly Asp Ala Gly Gly Pro Phe Val Met Lys
        290                 295                 300

Ser Pro Phe Asn Asn Arg Trp Tyr Gln Met Gly Ile Val Ser Trp Gly
305                 310                 315                 320

Glu Gly Cys Asp Arg Asp Gly Lys Tyr Gly Phe Tyr Thr His Val Phe
                325                 330                 335

Arg Leu Lys Lys Trp Ile Gln Lys Val Ile Asp Gln Phe Gly Glu
            340                 345                 350

<210> SEQ ID NO 13
<211> LENGTH: 1056
<212> TYPE: DNA
<213> ORGANISM: Homo sapiens
<220> FEATURE:
<221> NAME/KEY: CDS
<222> LOCATION: (1)..(1056)

<400> SEQUENCE: 13 atg gcg cac gtc cga ggc ttg cag ctg cct ggc tgc ctg gcc ctg gct      48
Met Ala His Val Arg Gly Leu Gln Leu Pro Gly Cys Leu Ala Leu Ala
1               5                   10                  15 gcc ctg tgt agc ctt gtg cac agc cag cat gtg ttc ctg gct cct cag      96
Ala Leu Cys Ser Leu Val His Ser Gln His Val Phe Leu Ala Pro Gln
            20                  25                  30 caa gca cgg tcg ctg ctc cag cgg gtc cgg cga acc gcc acc agt gag     144
Gln Ala Arg Ser Leu Leu Gln Arg Val Arg Arg Thr Ala Thr Ser Glu
        35                  40                  45 tac cag act ttc ttc aat ccg agg acc ttt ggc tcg gga gag gca gac     192
Tyr Gln Thr Phe Phe Asn Pro Arg Thr Phe Gly Ser Gly Glu Ala Asp
    50                  55                  60 tgt ggg ctg cga cct ctg ttc gag aag aag tcg ctg gag gac aaa acc     240
Cys Gly Leu Arg Pro Leu Phe Glu Lys Lys Ser Leu Glu Asp Lys Thr
65                  70                  75                  80 gaa aga gag ctc ctg gaa tcc tac atc gac ggg cgc att gtg gag ggc     288
Glu Arg Glu Leu Leu Glu Ser Tyr Ile Asp Gly Arg Ile Val Glu Gly
                85                  90                  95 tcg gat gca gag atc ggc atg tca cct tgg cag gtg atg ctt ttc cgg     336
Ser Asp Ala Glu Ile Gly Met Ser Pro Trp Gln Val Met Leu Phe Arg
            100                 105                 110 aag agt ccc cag gag ctg ctg tgt ggg gcc agc ctc atc agt gac cgc     384
Lys Ser Pro Gln Glu Leu Leu Cys Gly Ala Ser Leu Ile Ser Asp Arg
        115                 120                 125 tgg gtc ctc acc gcc gcc gcc tgc ctc ctg tac ccg ccc tgg gac aag     432
Trp Val Leu Thr Ala Ala Ala Cys Leu Leu Tyr Pro Pro Trp Asp Lys
    130                 135                 140 aac ttc acc gag aat gac ctt ctg gtg cgc att ggc acc cac tcc cgc     480
Asn Phe Thr Glu Asn Asp Leu Leu Val Arg Ile Gly Thr His Ser Arg
145                 150                 155                 160
```

-continued

| | | |
|---|---|---|
| aca agg tac gag cga aac att gaa aag ata tcc atg ttg gaa aag atc<br>Thr Arg Tyr Glu Arg Asn Ile Glu Lys Ile Ser Met Leu Glu Lys Ile<br>165                              170                            175 | | 528 |
| tac atc cac ccc agg tac aac tgg cgg gag aac ctg gac cgg gac att<br>Tyr Ile His Pro Arg Tyr Asn Trp Arg Glu Asn Leu Asp Arg Asp Ile<br>           180                           185                        190 | | 576 |
| gcc ctg atg aag ctg aag aag cct gtt gcc ttc agt gac tac att cac<br>Ala Leu Met Lys Leu Lys Lys Pro Val Ala Phe Ser Asp Tyr Ile His<br>195                              200                            205 | | 624 |
| cct gtg tgt ctg ccc gac agg gag acg gca gcc agc ttg ctc cag gct<br>Pro Val Cys Leu Pro Asp Arg Glu Thr Ala Ala Ser Leu Leu Gln Ala<br>      210                            215                        220 | | 672 |
| gga tac aag ggg cgg gtg aca ggc tgg ggc aac ctg aag gag acg tgg<br>Gly Tyr Lys Gly Arg Val Thr Gly Trp Gly Asn Leu Lys Glu Thr Trp<br>225                            230                          235                        240 | | 720 |
| aca gcc aac gtt ggt aag ggg cag ccc agt gtc ctg cag gtg gtg aac<br>Thr Ala Asn Val Gly Lys Gly Gln Pro Ser Val Leu Gln Val Val Asn<br>                      245                        250                        255 | | 768 |
| ctg ccc att gtg gag cgg ccg gtc tgc aag gac tcc acc cgg atc cgc<br>Leu Pro Ile Val Glu Arg Pro Val Cys Lys Asp Ser Thr Arg Ile Arg<br>                260                          265                        270 | | 816 |
| atc act gac aac atg ttc tgt gct ggt tac aag cct gat gaa ggg aaa<br>Ile Thr Asp Asn Met Phe Cys Ala Gly Tyr Lys Pro Asp Glu Gly Lys<br>275                              280                            285 | | 864 |
| cga ggg gat gcc tgt gaa ggg gac gcc ggg gga ccc ttt gtc atg aag<br>Arg Gly Asp Ala Cys Glu Gly Asp Ala Gly Gly Pro Phe Val Met Lys<br>      290                            295                        300 | | 912 |
| agc ccc ttt aac aac cgc tgg tat caa atg ggc atc gtc tca tgg ggt<br>Ser Pro Phe Asn Asn Arg Trp Tyr Gln Met Gly Ile Val Ser Trp Gly<br>305                            310                          315                        320 | | 960 |
| gaa ggc tgt gac cgg gat ggg aaa tat ggc ttc tac aca cat gtg ttc<br>Glu Gly Cys Asp Arg Asp Gly Lys Tyr Gly Phe Tyr Thr His Val Phe<br>                      325                        330                        335 | | 1008 |
| cgc ctg aag aag tgg ata cag aag gtc att gat cag ttt gga gag tag<br>Arg Leu Lys Lys Trp Ile Gln Lys Val Ile Asp Gln Phe Gly Glu<br>                  340                          345                        350 | | 1056 |

<210> SEQ ID NO 14
<211> LENGTH: 351
<212> TYPE: PRT
<213> ORGANISM: Homo sapiens

<400> SEQUENCE: 14

Met Ala His Val Arg Gly Leu Gln Leu Pro Gly Cys Leu Ala Leu Ala
1                  5                      10                      15

Ala Leu Cys Ser Leu Val His Ser Gln His Val Phe Leu Ala Pro Gln
                20                      25                      30

Gln Ala Arg Ser Leu Leu Gln Arg Val Arg Arg Thr Ala Thr Ser Glu
        35                      40                      45

Tyr Gln Thr Phe Phe Asn Pro Arg Thr Phe Gly Ser Gly Glu Ala Asp
    50                      55                      60

Cys Gly Leu Arg Pro Leu Phe Glu Lys Lys Ser Leu Glu Asp Lys Thr
65                  70                      75                      80

Glu Arg Glu Leu Leu Glu Ser Tyr Ile Asp Gly Arg Ile Val Glu Gly
                85                      90                      95

Ser Asp Ala Glu Ile Gly Met Ser Pro Trp Gln Val Met Leu Phe Arg
              100                      105                    110

Lys Ser Pro Gln Glu Leu Leu Cys Gly Ala Ser Leu Ile Ser Asp Arg
       115                      120                    125

```
Trp Val Leu Thr Ala Ala Cys Leu Leu Tyr Pro Pro Trp Asp Lys
    130                 135                 140

Asn Phe Thr Glu Asn Asp Leu Leu Val Arg Ile Gly Thr His Ser Arg
145                 150                 155                 160

Thr Arg Tyr Glu Arg Asn Ile Glu Lys Ile Ser Met Leu Glu Lys Ile
            165                 170                 175

Tyr Ile His Pro Arg Tyr Asn Trp Arg Glu Asn Leu Asp Arg Asp Ile
        180                 185                 190

Ala Leu Met Lys Leu Lys Lys Pro Val Ala Phe Ser Asp Tyr Ile His
            195                 200                 205

Pro Val Cys Leu Pro Asp Arg Glu Thr Ala Ala Ser Leu Leu Gln Ala
210                 215                 220

Gly Tyr Lys Gly Arg Val Thr Gly Trp Gly Asn Leu Lys Glu Thr Trp
225                 230                 235                 240

Thr Ala Asn Val Gly Lys Gly Gln Pro Ser Val Leu Gln Val Val Asn
                245                 250                 255

Leu Pro Ile Val Glu Arg Pro Val Cys Lys Asp Ser Thr Arg Ile Arg
            260                 265                 270

Ile Thr Asp Asn Met Phe Cys Ala Gly Tyr Lys Pro Asp Glu Gly Lys
        275                 280                 285

Arg Gly Asp Ala Cys Glu Gly Asp Ala Gly Gly Pro Phe Val Met Lys
290                 295                 300

Ser Pro Phe Asn Asn Arg Trp Tyr Gln Met Gly Ile Val Ser Trp Gly
305                 310                 315                 320

Glu Gly Cys Asp Arg Asp Gly Lys Tyr Gly Phe Tyr Thr His Val Phe
                325                 330                 335

Arg Leu Lys Lys Trp Ile Gln Lys Val Ile Asp Gln Phe Gly Glu
            340                 345                 350

<210> SEQ ID NO 15
<211> LENGTH: 1056
<212> TYPE: DNA
<213> ORGANISM: Homo sapiens
<220> FEATURE:
<221> NAME/KEY: CDS
<222> LOCATION: (1)..(1056)

<400> SEQUENCE: 15 atg gcg cac gtc cga ggc ttg cag ctg cct ggc tgc ctg gcc ctg gct    48
Met Ala His Val Arg Gly Leu Gln Leu Pro Gly Cys Leu Ala Leu Ala
1               5                   10                  15 gcc ctg tgt agc ctt gtg cac agc cag cat gtg ttc ctg gct cct cag    96
Ala Leu Cys Ser Leu Val His Ser Gln His Val Phe Leu Ala Pro Gln
            20                  25                  30 caa gca cgg tcg ctg ctc cag cgg gtc cgg cga acc gcc acc agt gag   144
Gln Ala Arg Ser Leu Leu Gln Arg Val Arg Arg Thr Ala Thr Ser Glu
        35                  40                  45 tac cag act ttc ttc aat ccg agg acc ttt ggc tcg gga gag gca gac   192
Tyr Gln Thr Phe Phe Asn Pro Arg Thr Phe Gly Ser Gly Glu Ala Asp
    50                  55                  60 tgt ggg ctg cga cct ctg ttc gag aag aag tcg ctg gag gac aaa acc   240
Cys Gly Leu Arg Pro Leu Phe Glu Lys Lys Ser Leu Glu Asp Lys Thr
65                  70                  75                  80 gaa aga gag ctc ctg gaa tcc tac atc gac ggg cgc att gtg gag ggc   288
Glu Arg Glu Leu Leu Glu Ser Tyr Ile Asp Gly Arg Ile Val Glu Gly
                85                  90                  95 tcg gat gca gag atc ggc atg tca cct tgg cag gtg atg ctt ttc cgg   336
Ser Asp Ala Glu Ile Gly Met Ser Pro Trp Gln Val Met Leu Phe Arg
            100                 105                 110
```

-continued

```
                            100                 105                 110
aag agt ccc cag gag ctg ctg tgt ggg gcc agc ctc atc agt gac cgc      384
Lys Ser Pro Gln Glu Leu Leu Cys Gly Ala Ser Leu Ile Ser Asp Arg
        115                 120                 125 tgg gtc ctc acc gcc gcc gcc tgc ctc ctg tac ccg ccc tgg gac aag      432
Trp Val Leu Thr Ala Ala Ala Cys Leu Leu Tyr Pro Pro Trp Asp Lys
130                 135                 140 aac ttc acc gag aat gac ctt ctg gtg cgc att ggc gcc cac tcc cgc      480
Asn Phe Thr Glu Asn Asp Leu Leu Val Arg Ile Gly Ala His Ser Arg
145                 150                 155                 160 aca agg tac gag cga aac att gaa aag ata tcc atg ttg gaa aag atc      528
Thr Arg Tyr Glu Arg Asn Ile Glu Lys Ile Ser Met Leu Glu Lys Ile
                165                 170                 175 tac atc cac ccc agg tac aac tgg cgg gag aac ctg gac cgg gac att      576
Tyr Ile His Pro Arg Tyr Asn Trp Arg Glu Asn Leu Asp Arg Asp Ile
            180                 185                 190 gcc ctg atg aag ctg aag aag cct gtt gcc ttc agt gac tac att cac      624
Ala Leu Met Lys Leu Lys Lys Pro Val Ala Phe Ser Asp Tyr Ile His
        195                 200                 205 cct gtg tgt ctg ccc gac agg gag acg gca gcc agc ttg ctc cag gct      672
Pro Val Cys Leu Pro Asp Arg Glu Thr Ala Ala Ser Leu Leu Gln Ala
    210                 215                 220 gga tac aag ggg cgg gtg aca ggc tgg ggc aac ctg aag gag acg tgg      720
Gly Tyr Lys Gly Arg Val Thr Gly Trp Gly Asn Leu Lys Glu Thr Trp
225                 230                 235                 240 aca gcc aac gtt ggt aag ggg cag ccc agt gtc ctg cag gtg gtg aac      768
Thr Ala Asn Val Gly Lys Gly Gln Pro Ser Val Leu Gln Val Val Asn
                245                 250                 255 ctg ccc att gtg gag cgg ccg gtc tgc aag gac tcc acc cgg atc cgc      816
Leu Pro Ile Val Glu Arg Pro Val Cys Lys Asp Ser Thr Arg Ile Arg
            260                 265                 270 atc act gac aac atg ttc tgt gct ggt tac aag cct gat gaa ggg aaa      864
Ile Thr Asp Asn Met Phe Cys Ala Gly Tyr Lys Pro Asp Glu Gly Lys
        275                 280                 285 cga ggg gat agt tgt gaa ggg gac gcc ggg gga ccc ttt gtc atg aag      912
Arg Gly Asp Ser Cys Glu Gly Asp Ala Gly Gly Pro Phe Val Met Lys
    290                 295                 300 agc ccc ttt aac aac cgc tgg tat caa atg ggc atc gtc tca tgg ggt      960
Ser Pro Phe Asn Asn Arg Trp Tyr Gln Met Gly Ile Val Ser Trp Gly
305                 310                 315                 320 gaa ggc tgt gac cgg gat ggg aaa tat ggc ttc tac aca cat gtg ttc     1008
Glu Gly Cys Asp Arg Asp Gly Lys Tyr Gly Phe Tyr Thr His Val Phe
                325                 330                 335 cgc ctg aag aag tgg ata cag aag gtc att gat cag ttt gga gag tag     1056
Arg Leu Lys Lys Trp Ile Gln Lys Val Ile Asp Gln Phe Gly Glu
            340                 345                 350

<210> SEQ ID NO 16
<211> LENGTH: 351
<212> TYPE: PRT
<213> ORGANISM: Homo sapiens

<400> SEQUENCE: 16

Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
                20                  25                  30

Gln Ala Arg Ser Leu Leu Gln Arg Val Arg Arg Thr Ala Thr Ser Glu
            35                  40                  45

Tyr Gln Thr Phe Phe Asn Pro Arg Thr Phe Gly Ser Gly Glu Ala Asp
```

```
            50                  55                  60
Cys Gly Leu Arg Pro Leu Phe Glu Lys Lys Ser Leu Glu Asp Lys Thr
 65                  70                  75                  80

Glu Arg Glu Leu Leu Glu Ser Tyr Ile Asp Gly Arg Ile Val Glu Gly
                 85                  90                  95

Ser Asp Ala Glu Ile Gly Met Ser Pro Trp Gln Val Met Leu Phe Arg
            100                 105                 110

Lys Ser Pro Gln Glu Leu Leu Cys Gly Ala Ser Leu Ile Ser Asp Arg
        115                 120                 125

Trp Val Leu Thr Ala Ala Cys Leu Leu Tyr Pro Pro Trp Asp Lys
130                 135                 140

Asn Phe Thr Glu Asn Asp Leu Leu Val Arg Ile Gly Ala His Ser Arg
145                 150                 155                 160

Thr Arg Tyr Glu Arg Asn Ile Glu Lys Ile Ser Met Leu Glu Lys Ile
                165                 170                 175

Tyr Ile His Pro Arg Tyr Asn Trp Arg Glu Asn Leu Asp Arg Asp Ile
            180                 185                 190

Ala Leu Met Lys Leu Lys Lys Pro Val Ala Phe Ser Asp Tyr Ile His
        195                 200                 205

Pro Val Cys Leu Pro Asp Arg Glu Thr Ala Ala Ser Leu Leu Gln Ala
210                 215                 220

Gly Tyr Lys Gly Arg Val Thr Gly Trp Gly Asn Leu Lys Glu Thr Trp
225                 230                 235                 240

Thr Ala Asn Val Gly Lys Gly Gln Pro Ser Val Leu Gln Val Val Asn
                245                 250                 255

Leu Pro Ile Val Glu Arg Pro Val Cys Lys Asp Ser Thr Arg Ile Arg
            260                 265                 270

Ile Thr Asp Asn Met Phe Cys Ala Gly Tyr Lys Pro Asp Glu Gly Lys
        275                 280                 285

Arg Gly Asp Ser Cys Glu Gly Asp Ala Gly Gly Pro Phe Val Met Lys
        290                 295                 300

Ser Pro Phe Asn Asn Arg Trp Tyr Gln Met Gly Ile Val Ser Trp Gly
305                 310                 315                 320

Glu Gly Cys Asp Arg Asp Gly Lys Tyr Gly Phe Tyr Thr His Val Phe
                325                 330                 335

Arg Leu Lys Lys Trp Ile Gln Lys Val Ile Asp Gln Phe Gly Glu
            340                 345                 350

<210> SEQ ID NO 17
<211> LENGTH: 1056
<212> TYPE: DNA
<213> ORGANISM: Homo sapiens
<220> FEATURE:
<221> NAME/KEY: CDS
<222> LOCATION: (1)..(1056)

<400> SEQUENCE: 17 atg gcg cac gtc cga ggc ttg cag ctg cct ggc tgc ctg gcc ctg gct      48
Met Ala His Val Arg Gly Leu Gln Leu Pro Gly Cys Leu Ala Leu Ala
 1               5                  10                  15 gcc ctg tgt agc ctt gtg cac agc cag cat gtg ttc ctg gct cct cag      96
Ala Leu Cys Ser Leu Val His Ser Gln His Val Phe Leu Ala Pro Gln
            20                  25                  30 caa gca cgg tcg ctg ctc cag cgg gtc cgg cga acc gcc acc agt gag     144
Gln Ala Arg Ser Leu Leu Gln Arg Val Arg Arg Thr Ala Thr Ser Glu
        35                  40                  45
```

| | |
|---|---|
| tac cag act ttc ttc aat ccg agg acc ttt ggc tcg gga gag gca gac<br>Tyr Gln Thr Phe Phe Asn Pro Arg Thr Phe Gly Ser Gly Glu Ala Asp<br>    50                          55                    60 | 192 |
| tgt ggg ctg cga cct ctg ttc gag aag aag tcg ctg gag gac aaa acc<br>Cys Gly Leu Arg Pro Leu Phe Glu Lys Lys Ser Leu Glu Asp Lys Thr<br>65                      70                    75                    80 | 240 |
| gaa aga gag ctc ctg gaa tcc tac atc gac ggg cgc att gtg gag ggc<br>Glu Arg Glu Leu Leu Glu Ser Tyr Ile Asp Gly Arg Ile Val Glu Gly<br>                    85                    90                    95 | 288 |
| tcg gat gca gag atc ggc atg tca cct tgg cag gtg atg ctt ttc cgg<br>Ser Asp Ala Glu Ile Gly Met Ser Pro Trp Gln Val Met Leu Phe Arg<br>               100                   105                 110 | 336 |
| aag agt ccc cag gag ctg ctg tgt ggg gcc agc ctc atc agt gac cgc<br>Lys Ser Pro Gln Glu Leu Leu Cys Gly Ala Ser Leu Ile Ser Asp Arg<br>           115                   120                 125 | 384 |
| tgg gtc ctc acc gcc gcc gcc tgc ctc ctg tac ccg ccc tgg gac aag<br>Trp Val Leu Thr Ala Ala Ala Cys Leu Leu Tyr Pro Pro Trp Asp Lys<br>    130                   135                 140 | 432 |
| aac ttc acc gag aat gac ctt ctg gtg cgc att ggc gcc cac tcc cgc<br>Asn Phe Thr Glu Asn Asp Leu Leu Val Arg Ile Gly Ala His Ser Arg<br>145                   150                 155                 160 | 480 |
| aca agg tac gag cga aac att gaa aag ata tcc atg ttg gaa aag atc<br>Thr Arg Tyr Glu Arg Asn Ile Glu Lys Ile Ser Met Leu Glu Lys Ile<br>               165                   170                 175 | 528 |
| tac atc cac ccc agg tac aac tgg cgg gag aac ctg gac cgg gac att<br>Tyr Ile His Pro Arg Tyr Asn Trp Arg Glu Asn Leu Asp Arg Asp Ile<br>           180                   185                 190 | 576 |
| gcc ctg atg aag ctg aag aag cct gtt gcc ttc agt gac tac att cac<br>Ala Leu Met Lys Leu Lys Lys Pro Val Ala Phe Ser Asp Tyr Ile His<br>               195                   200                 205 | 624 |
| cct gtg tgt ctg ccc gac agg gag acg gca gcc agc ttg ctc cag gct<br>Pro Val Cys Leu Pro Asp Arg Glu Thr Ala Ala Ser Leu Leu Gln Ala<br>    210                 215                 220 | 672 |
| gga tac aag ggg cgg gtg aca ggc tgg ggc aac ctg aag gag acg tgg<br>Gly Tyr Lys Gly Arg Val Thr Gly Trp Gly Asn Leu Lys Glu Thr Trp<br>225                   230                 235                 240 | 720 |
| aca gcc aac gtt ggt aag ggg cag ccc agt gtc ctg cag gtg gtg aac<br>Thr Ala Asn Val Gly Lys Gly Gln Pro Ser Val Leu Gln Val Val Asn<br>               245                   250                 255 | 768 |
| ctg ccc att gtg gag cgg ccg gtc tgc aag gac tcc acc cgg atc cgc<br>Leu Pro Ile Val Glu Arg Pro Val Cys Lys Asp Ser Thr Arg Ile Arg<br>           260                   265                 270 | 816 |
| atc act gac aac atg ttc tgt gct ggt tac aag cct gat gaa ggg aaa<br>Ile Thr Asp Asn Met Phe Cys Ala Gly Tyr Lys Pro Asp Glu Gly Lys<br>    275                 280                 285 | 864 |
| gcc ggg gat gcc tgt gaa ggg gac gcc ggg gga ccc ttt gtc atg aag<br>Ala Gly Asp Ala Cys Glu Gly Asp Ala Gly Gly Pro Phe Val Met Lys<br>290                   295                 300 | 912 |
| agc ccc ttt aac aac cgc tgg tat caa atg ggc atc gtc tca tgg ggt<br>Ser Pro Phe Asn Asn Arg Trp Tyr Gln Met Gly Ile Val Ser Trp Gly<br>305                   310                 315                 320 | 960 |
| gaa ggc tgt gac cgg gat ggg aaa tat ggc ttc tac aca cat gtg ttc<br>Glu Gly Cys Asp Arg Asp Gly Lys Tyr Gly Phe Tyr Thr His Val Phe<br>               325                   330                 335 | 1008 |
| cgc ctg aag aag tgg ata cag aag gtc att gat cag ttt gga gag tag<br>Arg Leu Lys Lys Trp Ile Gln Lys Val Ile Asp Gln Phe Gly Glu<br>           340                   345                 350 | 1056 |

<210> SEQ ID NO 18
<211> LENGTH: 351
<212> TYPE: PRT
<213> ORGANISM: Homo sapiens

<400> SEQUENCE: 18

Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Thr Ala Thr Ser Glu
        35                  40                  45

Tyr Gln Thr Phe Phe Asn Pro Arg Thr Phe Gly Ser Gly Glu Ala Asp
    50                  55                  60

Cys Gly Leu Arg Pro Leu Phe Glu Lys Lys Ser Leu Glu Asp Lys Thr
65                  70                  75                  80

Glu Arg Glu Leu Leu Glu Ser Tyr Ile Asp Gly Arg Ile Val Glu Gly
                85                  90                  95

Ser Asp Ala Glu Ile Gly Met Ser Pro Trp Gln Val Met Leu Phe Arg
            100                 105                 110

Lys Ser Pro Gln Glu Leu Leu Cys Gly Ala Ser Leu Ile Ser Asp Arg
        115                 120                 125

Trp Val Leu Thr Ala Ala Cys Leu Leu Tyr Pro Pro Trp Asp Lys
    130                 135                 140

Asn Phe Thr Glu Asn Asp Leu Leu Val Arg Ile Gly Ala His Ser Arg
145                 150                 155                 160

Thr Arg Tyr Glu Arg Asn Ile Glu Lys Ile Ser Met Leu Glu Lys Ile
                165                 170                 175

Tyr Ile His Pro Arg Tyr Asn Trp Arg Glu Asn Leu Asp Arg Asp Ile
            180                 185                 190

Ala Leu Met Lys Leu Lys Lys Pro Val Ala Phe Ser Asp Tyr Ile His
        195                 200                 205

Pro Val Cys Leu Pro Asp Arg Glu Thr Ala Ala Ser Leu Leu Gln Ala
    210                 215                 220

Gly Tyr Lys Gly Arg Val Thr Gly Trp Gly Asn Leu Lys Glu Thr Trp
225                 230                 235                 240

Thr Ala Asn Val Gly Lys Gly Gln Pro Ser Val Leu Gln Val Val Asn
                245                 250                 255

Leu Pro Ile Val Glu Arg Pro Val Cys Lys Asp Ser Thr Arg Ile Arg
            260                 265                 270

Ile Thr Asp Asn Met Phe Cys Ala Gly Tyr Lys Pro Asp Glu Gly Lys
        275                 280                 285

Ala Gly Asp Ala Cys Glu Gly Asp Ala Gly Gly Pro Phe Val Met Lys
    290                 295                 300

Ser Pro Phe Asn Asn Arg Trp Tyr Gln Met Gly Ile Val Ser Trp Gly
305                 310                 315                 320

Glu Gly Cys Asp Arg Asp Gly Lys Tyr Gly Phe Tyr Thr His Val Phe
                325                 330                 335

Arg Leu Lys Lys Trp Ile Gln Lys Val Ile Asp Gln Phe Gly Glu
            340                 345                 350